(12) United States Patent
Schwartz et al.

(10) Patent No.: US 8,271,427 B1
(45) Date of Patent: Sep. 18, 2012

(54) COMPUTER DATABASE SYSTEM FOR SINGLE MOLECULE DATA MANAGEMENT AND ANALYSIS

(75) Inventors: David Charles Schwartz, Madison, WI (US); Christopher P. Churas, Madison, WI (US); Galex S. Yen, Sammamish, WA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 143 days.

(21) Appl. No.: 12/686,478

(22) Filed: Jan. 13, 2010

(51) Int. Cl.
G06F 7/00 (2006.01)
G06F 19/00 (2011.01)

(52) U.S. Cl. .......... 707/600; 702/19; 707/705; 707/790

(58) Field of Classification Search .................. None
See application file for complete search history.

(56) References Cited

U.S. PATENT DOCUMENTS

| | | | |
|---|---|---|---|
| 4,695,548 A | 9/1987 | Cantor et al. | |
| 6,294,136 B1 | 9/2001 | Schwartz | |
| 6,453,333 B1 * | 9/2002 | Glynias et al. | 709/202 |
| 6,804,679 B2 * | 10/2004 | Jevons et al. | 1/1 |
| 2002/0091490 A1 | 7/2002 | Russo et al. | 702/19 |
| 2003/0009099 A1 * | 1/2003 | Lett et al. | 600/416 |

OTHER PUBLICATIONS

North et al. (Proceedings of the IEEE Symposium on Information Visualization 2002 (InfoVis'02) (2002), The Computer Society, pp. 1-8).*
Bahl et al. Nucleic Acids Research, vol. 30, pp. 87-90, Jan. 2002.
Consortium. Nucleic Acids Research, vol. 29, pp. 66-69, Jan. 2001.
Lai et al. Nature Genetics, vol. 23, pp. 309-313, 1999.
Christopher Aston et al., "Optical Mapping: An Approach for Fine Mapping", Methods in Enzymol, 1999, pp. 55-73, vol. 303.
Christopher Aston et al., "Optical Mapping and its Potential for Large-Scale Sequencing Projects, Trends in Biotechnology", 1999, pp. 297-302, vol. 17.
Weiwen Cai et al., "Ordered Restriction Endonuclease Maps of Yeast Artificial Chromosomes Created by Optical Mapping on Surfaces", Proc. Natl. Acad. Sci., May 1995, pp. 5164-5168, vol. 92.
Weiwen Cai et al., "High-resolution Restriction Maps of Bacterial Artificial Chromosomes Constructed by Optical Mapping", Proc. Natl. Acad. Sci., Mar. 1998, pp. 3390-3395, vol. 95.
Joseph Giacalone et al., "Optical Mapping of BAC Clones from the Human Y Chromosome DAZ Locus", Genome Research, 2000, pp. 1421-1429, vol. 10.
Junping Jing et al., "Automated High Resolution Optical Mapping Using Arrayed, Fluid-Fixed DNA Molecules", Proc. Natl. Acad. Sci, Jul. 1998, pp. 8046-8051, vol. 95.
Eric S. Lander et al., "Genomic Mapping by Fingerprinting Random Clones: A Mathematical Analysis", Genomics, 1988, pp. 231-239, vol. 2.
Xun Meng et al., "Optical Mapping of Lambda Bacteriophage Clones Using Restriction Endonucleases", Nature Genetics, Apr. 1995, pp. 432-438, vol. 9.
Akhtar Samad et al., "Optical Mapping: A Novel, Single-Molecule Approach to Genomic Analysis", Genome Research, 1995, pp. 1-4, vol. 5.
Akhtar H. Samad et al., "Mapping the Genome One Molecule at a Time—Optical Mapping", Nature, Nov. 30, 1995, pp. 516-517, vol. 378.
David C. Schwartz et al., "Separation of Yeast Chromosome-Sized DNAs by Pulsed Field Gradient Gel Electrophoresis", Cell, May 1984, pp. 67-75, vol. 37.
John Skiadas et al., "Optical PCR: Genomic Analysis by Long-Range PCR and Optical Mapping", Mammalian Genome, 1999, pp. 1005-1009, vol. 10.
Heng Zhu et al., "Global Analysis of Protein Activities Using Proteome Chips", Science, Sep. 14, 2001, pp. 2101-2105, vol. 293.

* cited by examiner

*Primary Examiner* — Lori A Clow
(74) *Attorney, Agent, or Firm* — Quarles & Brady LLP

(57) ABSTRACT

A computer database system for storing, processing, displaying, and analyzing single molecule data is capable of managing and processing variously formatted, different kinds of single molecule data and displaying subsets thereof upon instructions by a user. A component-based architecture is implemented where the processing and the displaying are separately performed. The data is dynamically loaded for processing as needed. Embodiments of computer database systems can be utilized in managing single molecule data, particularly image data derived from single molecule images. Such single molecule images may be generated by a variety of technologies, e.g., optical mapping, atomic force microscopy (AFM), scanning tunneling microscopy (STM), and flow cytometry. Systems may be deployed over a computer network. One or more additional databases may be included which are interconnected through a network.

15 Claims, 5 Drawing Sheets

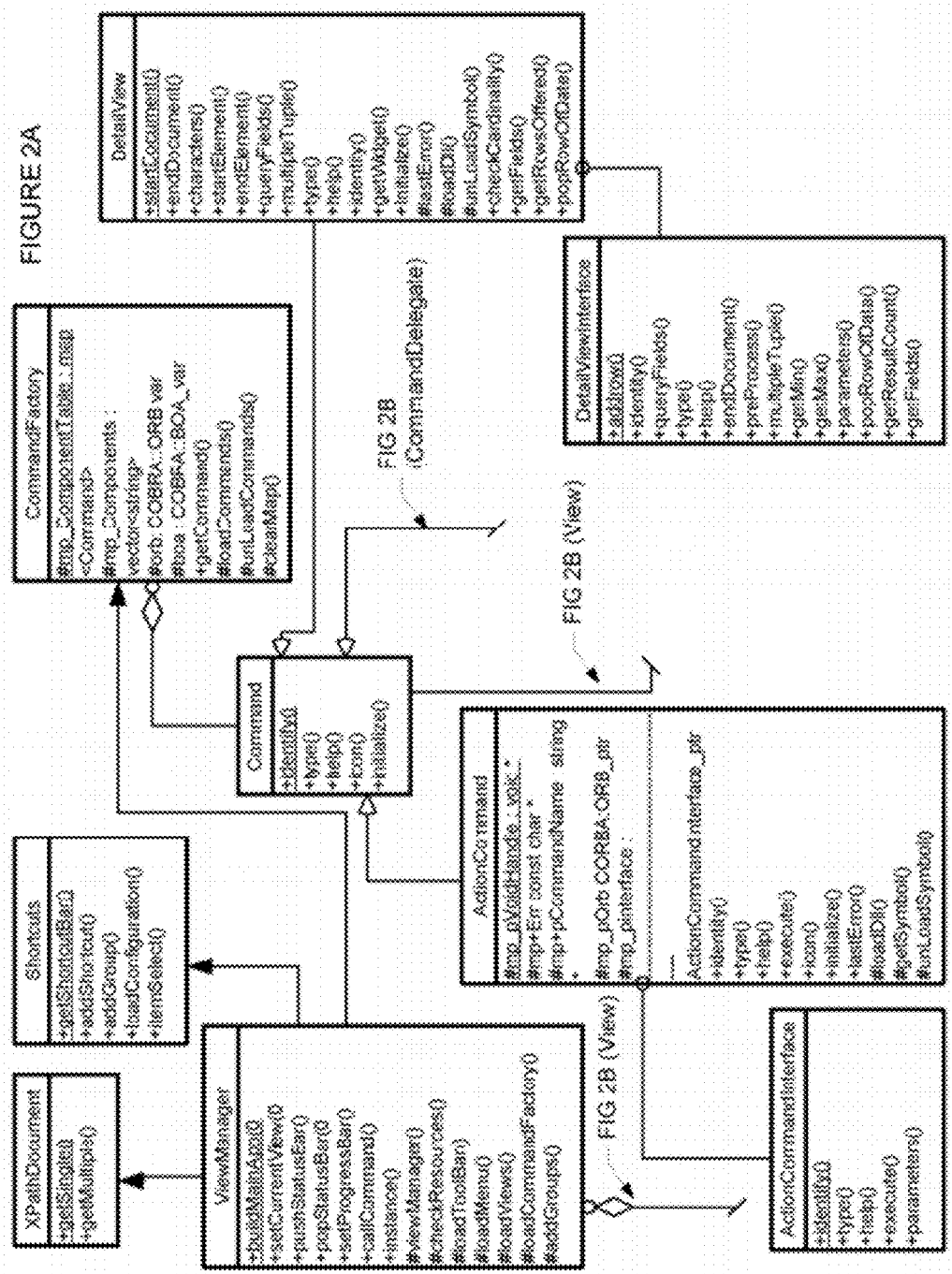

COMPUTER DATABASE SYSTEM FOR SINGLE MOLECULE DATA MANAGEMENT AND ANALYSIS

STATEMENT REGARDING FEDERALLY SPONSORED RESEARCH. OR DEVELOPMENT

This invention was made with United States government support awarded by the following agencies: DOE DE-FG02-99ER62830. The United States government has certain rights in this invention.

CROSS-REFERENCE TO RELATED APPLICATION

This application claims priority to non-provisional U.S. patent application Ser. No. 12/509,743, filed on Jul. 27, 2009, which claims priority to U.S. patent application Ser. No. 10/777,850, filed on Feb. 13, 2004, which claims priority to U.S. Provisional Application No. 60/447,293, filed Feb. 14, 2003, the contents of which are expressly incorporated herein by reference.

BACKGROUND OF THE DISCLOSURE

This disclosure relates in general to data management and analysis. Embodiments of this disclosure relate to management and analysis of single molecule data, i.e., data on individual macromolecules such as nucleic acid and protein molecules. Further, embodiments of this disclosure provide computer database systems for storing, processing, displaying, and analyzing single molecule data such as data from optical mapping of single molecules. Hence, embodiments described herein enable comprehensive data analysis in genomics and proteomics involving a wide array of differently formatted single molecule data.

The availability of whole genome sequences of an increased number of species brings genomics and proteomics in the forefront of the modern biomedical sciences and marks a new era of research and development in the healthcare, food, and cosmetic industries, among others. While promising unprecedented potential in understanding the genetic make up of different species and the mechanisms of life, the massive amount of sequence data poses a significant challenge of data management, analysis, and knowledge extraction to biomedical researchers. One notable factor constituting such challenge is the diverse data formats. These data are derived from a variety of technology platforms, including, e.g., automated sequencing, full length DNA cloning, in-situ hybridization of nucleotide and peptide molecules, nucleic acid and protein arrays, and microfluidics, etc. Even with the same platform, different device models and/or different protocols operated in various laboratories or institutions often produce data with different format and different resolution or sensitivity, which calls for different annotative and interpretative approaches for further processing. Effective methods and systems are therefore needed to manage these different kinds or different types of data and to enable discovery of interrelations among them, such that useful knowledge can be extracted on the individual and collective functions of the proteins and nucleic acids of interest. Ultimately, such systems and methods are required for the realization of the promises held by the genomics and proteomics technologies.

In recent years, methodologies and instruments have been developed that permit study of individual macromolecules, i.e., DNA, RNA, and proteins. Single molecule optical mapping is one such effective approach for close and direct analysis of single molecules. See, U.S. Pat. No. 6,294,136, the disclosure of which is fully incorporated herein by reference. Any data generated from such studies—e.g., by manipulating and observing single molecules—constitutes single molecule data. The single molecule data thus comprise, among other things, single molecule images, physical characteristics such as lengths and shapes of single molecules, sequences of the single molecules, and restriction maps of single molecules. Such single molecule data complements genomics and proteomics data generated from the other technology platforms and provides new insights into the structure and functionalities of genomes and their constitutive functional units.

The usefulness of the single molecule data is accompanied by the heightened challenge of its management and analysis. This is due, in part, to the aspect of image processing and restriction map construction involved with single molecule images. For example, typically in optical mapping, visible gap sites on a single DNA molecules may be recorded and the mass of a DNA fragment defined by these gaps is determined by integrated fluorescence measurements and length measurements through image analysis; and subsequently, a restriction map may be derived. Such restriction map provides a road map in understanding the structure and function of the DNA of interest and may be used to compare with and validate the results of physical mapping, among other things.

There is therefore a need for systems capable of storing, processing, and analyzing image data of single molecules, which systems at the same time are capable of processing and analyzing other types of single molecule data, as well as other kinds of biomedical data. Such systems should support comprehensive genomic and proteomic data analysis across technology platforms, allowing image data to be correlated with non-image data. The robustness and flexibility for handling diverse data formats are desired, as is fast user response.

SUMMARY

It is therefore an object of this disclosure to provide computer database systems for storing, processing, displaying, and analyzing single molecule data. Particularly, the database systems disclosed in various embodiments herein are capable of managing and processing variously formatted, different kinds of single molecule data and displaying subsets thereof upon instructions by a user. These database systems offer improved flexibility and ease in fast data handling and user response. They enable comprehensive analysis of single molecule data, alone or in conjunction with other types of biomedical data. A component-based architecture is implemented where the processing and the displaying are separately performed. The data is dynamically loaded for processing as needed.

In accordance with one embodiment, there is provided a computer database system for managing and analyzing data from single molecule images, wherein the single molecule images comprise signals derived from individual molecules or individual molecular assemblies or polymers, which method comprises: a database capable of storing single molecule data, which single molecule data comprises data from single molecule images; and a user interface capable of displaying the single molecule data.

According to one embodiment, the signals are optical, atomic, or electronic. According to another embodiment, the signals are generated by atomic force microscopy, tunneling electronic microscopy, flow cytometry, optical mapping, or near field microscopy.

According to another embodiment, the single molecule images are derived from optical mapping of single molecules, wherein the single molecules are individual molecules or individual molecular assemblies or polymers.

According to another embodiment, the single molecules are nucleic acid molecules or protein molecules.

According to another embodiment, the single molecule data in the computer system further comprises one or more restriction maps. According to yet another embodiment, the single molecule data further comprises one or more sequences. According to still another embodiment, the sequences are nucleotide sequences or amino acid sequences.

According to another embodiment, the database comprises one or more data files. According to yet another embodiment, the database is a relational database. According to still another embodiment, the database is an object database.

According to another embodiment, the computer database system further comprises a processor capable of processing the single molecule data, the processor interacts with the user interface. According to yet another embodiment, the processor is capable of processing (0 one or more instructions from a user or (ii) one or more predetermined internal commands and having a subset of the single molecule data selectively displayed by the user interface. According to still another embodiment, the subset is selected from the group consisting of one or more single molecule images, restriction maps, sequences, and any combinations thereof. According to a further embodiment, the instructions and commands of processing are dynamically loaded such that the processing by the processor is separated from and independent of the displaying by the user interface. According to a still further embodiment, the computer database system is further capable of accepting instructions from a user and displaying new subsets of the single molecule data, wherein the new subsets are newly compiled in the computer database system.

According to another embodiment, the computer database system is implemented and deployed over a computer network.

According to yet another embodiment, the database of the system is capable of storing other biomedical data, wherein the other biomedical data is derived from one or more biomedical technology platforms, wherein the computer database system is further capable of managing and analyzing other biomedical data.

According to still another embodiment, the computer database system further comprises one or more additional databases capable of storing single molecule data or other biomedical data, wherein the other biomedical data is derived from one or more biomedical technology platforms. In a further embodiment, the database and the one or more additional databases are connected via a computer network.

In accordance with this disclosure, there is provided, in another embodiment, a data structure capable of being stored on a computer-readable medium, the data structure comprises single molecule data, such as those generated from optical mapping of single molecules.

According to one embodiment, these single molecules are nucleic acid molecules or a protein molecules.

According to another embodiment, the single molecule data comprises one or more single molecule images. According to yet another embodiment, the single molecule data further comprises one or more restriction maps. According to still another embodiment, the single molecule data further comprises one or more sequences. According to a further embodiment, the sequences are nucleotide sequences or amino acid sequences.

BRIEF DESCRIPTION OF DRAWINGS

FIGS. 2A-B are a UML (Unified Modeling Language) diagram showing various components of the computer database system according to one embodiment of this disclosure.

DETAILED DESCRIPTION

Brief Discussion of Relevant Terms

Figure 1A:
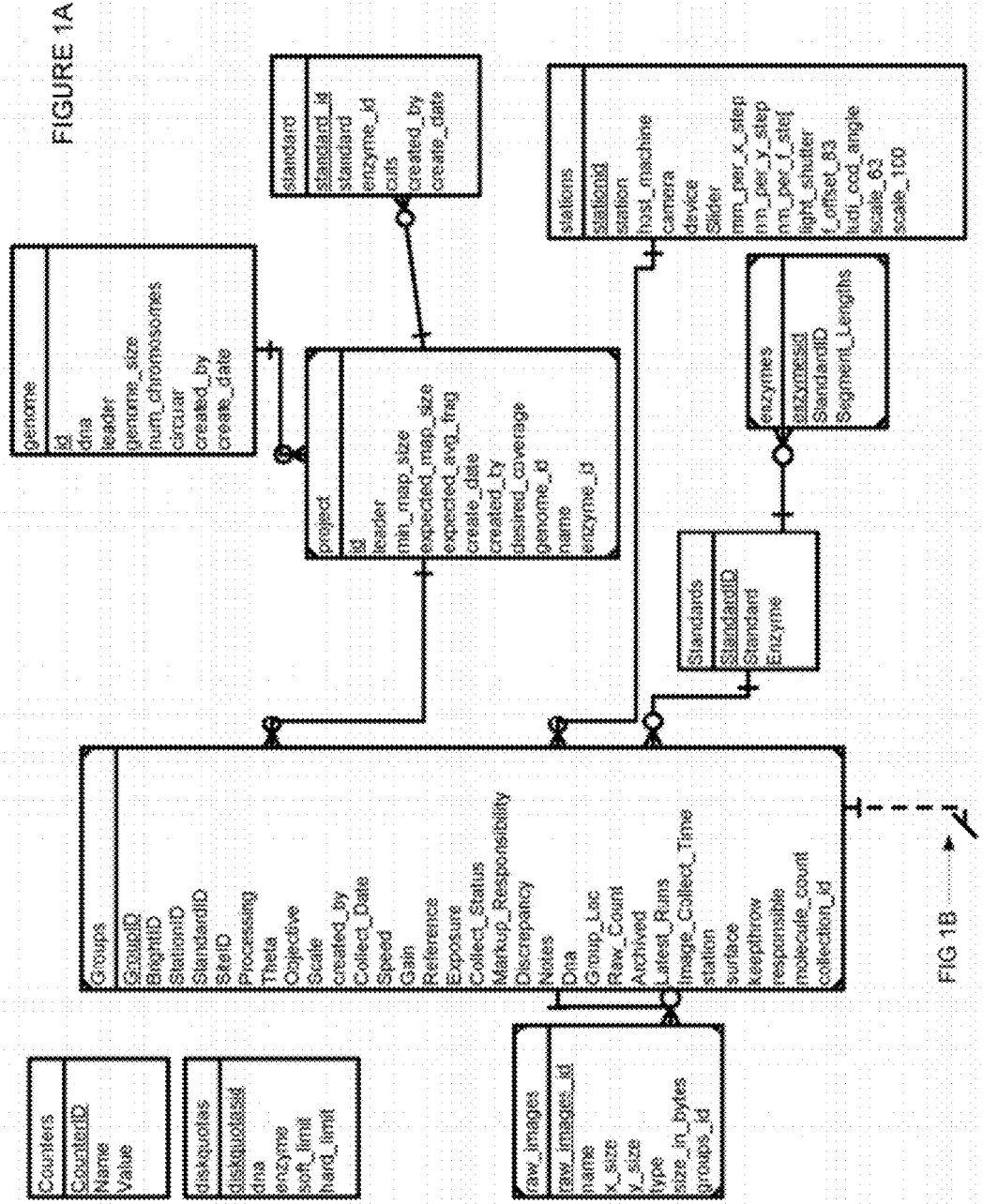
FIGS. 1A-B are an entity-relationship diagram depicting the database schema of the computer database system according to one embodiment of this disclosure.

The following disciplines, molecular biology, microbiology, immunology, virology, pharmaceutical chemistry, medicine, histology, anatomy, pathology, genetics, ecology, computer sciences, statistics, mathematics, chemistry, physics, material sciences, and artificial intelligence, are to be understood consistently with their typical meanings established in the relevant art.

As used herein, genomics refers to studies of nucleic acid sequences and applications of such studies in biology and medicine; proteomics refers to studies of protein sequences, conformation, structure, protein physical and chemical properties, and applications of such studies in biology and medicine; cheminformatics refers to the convergence of biopharmaceutical chemistry and information sciences, namely, the application of information technologies in biopharmaceutical chemistry; bioinformatics refers to the convergence of biomedical sciences and information sciences, namely, the application of information technologies in biomedical sciences; and phamacogenomics refers to the application of genomics in biopharmaceutical research, discovery, and product development.

The following terms, proteins, nucleic acids, DNA, RNA, genes, macromolecules, restriction enzymes, restriction maps, physical mapping, optical mapping, hybridization, 20 sequencing, sequence homology, expressed sequence tags (ESTs), single nucleotide polymorphism (SNP), and clustering, are to be understood consistently with their commonly accepted meanings in the relevant art, i.e., the art of molecular biology, genomics, and proteomics.

The following terms, atomic force microscopy (AFM), scanning tunneling microscopy (STM), flow cytometry, optical mapping, and near field microscopy, etc., are to be understood consistently with their commonly accepted meanings in the relevant art, i.e., the art of physics, biology, material sciences, and surface sciences.

The following terms, database, database server, database schema, entity-relationship diagram, Unified Modeling Language (UML), Extensible Markup Language (XML), SQL, as used herein, are to be understood consistently with their commonly accepted meanings in the relevant art, i.e., the art of computer sciences and information management.

As used herein, single molecules refer to any individual molecules, such as macromolecule nucleic acids and proteins. A single molecule according to this disclosure may be an individual molecule or individual molecular assembly or polymer. That is, for example, a single peptide molecule comprises many individual amino acids. Thus, the terms "single molecule," "individual molecule," "individual molecular assembly," and "individual molecular polymer" are used interchangeably in various embodiments of this disclosure. Single molecule data refers to any data about or relevant to single molecules or individual molecules. Such data may be derived from studying single molecules using a variety of technology platforms, e.g., flow cytometry and optical mapping. The single molecule data thus comprise, among other things, single molecule images, physical characteristics such as lengths, heights, dimensionalities, charge densities, conductivity, capacitance, resistance of single molecules, sequences of single molecules, structures of single molecules, and restriction maps of single molecules.

Single molecule images according to various embodiments comprise signals derived from single Molecules, individual molecules, or individual molecule assemblies and polymers; such signals may be optical, atomic, or electronic, among other things. For example, a single molecule image may be generated by, inter alia, atomic force microscopy (AFM), flow cytometry, optical mapping, and near field microscopy. Thus, electronic, optical, and atomic probes may be used in producing single molecule images according to various embodiments. In certain embodiments, various wavelengths may be employed when light microscopy is used to generate single molecule images, including, e.g., laser, UV, near and far red. In other embodiments, various fluorophore may be employed when fluorescent signals are acquired. Further, single molecule images according to various embodiments of this disclosure may be multi-spectral and multi-dimensional (e.g., one, two, three-dimensional).

As used herein, genomics and proteomics data refers to any data generated in genomics and proteomics studies from different technology platforms; and biomedical data refers to data derived from any one or more biomedical technology platforms.

As used herein, the term "contig" refers to a nucleotide (e.g., DNA) whose sequence is derived by clustering a collection of smaller nucleotide (e.g., DNA) sequences that share certain level of sequence homology. Typically, one manages to obtain a full-length DNA sequence by building longer and longer contigs from known sequences of smaller DNA (or RNA) fragments (such as expressed sequence tags, ESTs) by performing clustering and assembly. Various clustering programs are known; some of which are publicly available. See, e.g., "CluserW" and "Fragment Assembler".

The term "array" or "microarray" refers to nucleotide or protein arrays; "array," "slide," and "chip" are interchangeable where used in this disclosure. Various kinds of to nucleotide arrays are made in research and manufacturing facilities worldwide, some of which are available commercially. (e.g., GeneChip™ by Affymetrix, Inc., LifeArray™ by Incyte Genomics). Protein chips are also widely used. See Zhu et al., Science 293(5537):2101-05, 2001.

A user interface, or a viewer, as used herein and interchangeably, refers to any kind of computer application or program that enables interactions with a user. A user interface or viewer may be a graphical user interface (GUI), such as a browser. Examples of such a browser include Microsoft Internet Explorer™ and Netscape Navigator™. A user interface also may be a simple command line interface in alternative embodiments. A user interface according to this disclosure may also include plug-in tools that extend the existing applications and support interaction with standard desktop applications. A user interface in certain embodiments of this disclosure may be designed to best support users' browsing activities according to ergonomic principles. A user interface or a viewer may present different views of the data in various embodiments according to this disclosure.

Database Schema and the Robustness of the Computer Database System

The database schema of the computer database system is designed according to embodiments of this disclosure to handle a multitude of data types and data formats. Such flexibility lends the desired robustness to the computer database systems according to this disclosure. A diverse collection of single molecule data, proteomics and genomics data, and other biomedical data generated from different technology platforms are represented and accounted for by the corresponding entities in the database system. An entity has one or more attributes which define its identity; the attributes bear certain values which quantitatively determine the characteristic or state of the entity. Each entity relates to one or more other entities through relationships, properly defined where applicable. Linked together, an information-enriched network of entities is thus established. This network is a resilient network because it expands as new entities are constructed and linked in and it grows as new attributes are added for the existing entities. The relationships among entities also may be adjusted such that the collective state of a set of interrelated entities may evolve or mature over time or upon change of certain conditions. Hence, the information network captured by the database according to the instant disclosure not static, but dynamic. The correlations and interactions (e.g., agonistic or antagonistic reactions) among the entities can thus be tracked and studied.

The design or definition of an entity and its attributes is keyed to the kind of data it is to represent and the underlining technology. For example, optical mapping has been used to prepare restriction maps of a variety of clone types. See, e.g., Giacalone, J, et al., *Genome Research* 10: 1421-1429, 2000; Skiadas, J., et al., *Mammalian Genome*, 10:1005-1009, 1999; Aston, C., *Trends in Biotechnology*, 17: 297-302, 1999; Aston, C., *Methods in Enzymol.*, 303: 55-73, 1999; Cal, W., *Proc. Natl. Acad. Sci. USA*, 95: 3390-3395, 1998; Jing, J., *Proc. Natl. Acad. Sci. USA*, 95: 8046-8051, 1998; Samad, A. H., *Nature*, 378: 516-517, 1995; Samad, A., *Genome Research*, 5: 1-4, 1995; Cal, W., *Proc. Natl. Acad. Sci. USA*, 92: 5164-5168, 1995; Meng, X., *Nature Genetics*, 9: 432-438, 1995.

The clones can be mounted intact on open derivatized optical mapping surfaces. Large genomic DNA molecules may be analyzed similarly by optical mapping when usable distribution of molecular extension and minimal breakages are applied. Genomic DNA may be isolated from cells embedded in low melting point agarose gel inserts which are treated with proteinase K and detergents. Known methods for minimizing shearing may be utilized to enhance the quality of the DNA molecules for direct measurements. See, e.g., Schwartz, D. et al., *Cell*, 37: 67-75, 1984; U.S. Pat. No. 4,695,548. Increasing the size of measurable molecules decreases the number required for mapping a complete genome. See, Lander and Waterman 1988. See, e.g., Lander E S 20 and Waterman M S, *Genomics* 2(3):231-9, April 1988. A set of DNA fragment molecules may be assembled together to form a contig, which in turn represents the full-length DNA of interest. The restriction map built through optical mapping reflects such assembly process. Therefore, embodiments of database systems of this disclosure are designed to cover the genomics and proteomics experiments such as optical mapping and, to support the data generated by various technologies, including, e.g., restriction maps, sequences, contigs, and images.

Figure 1B:
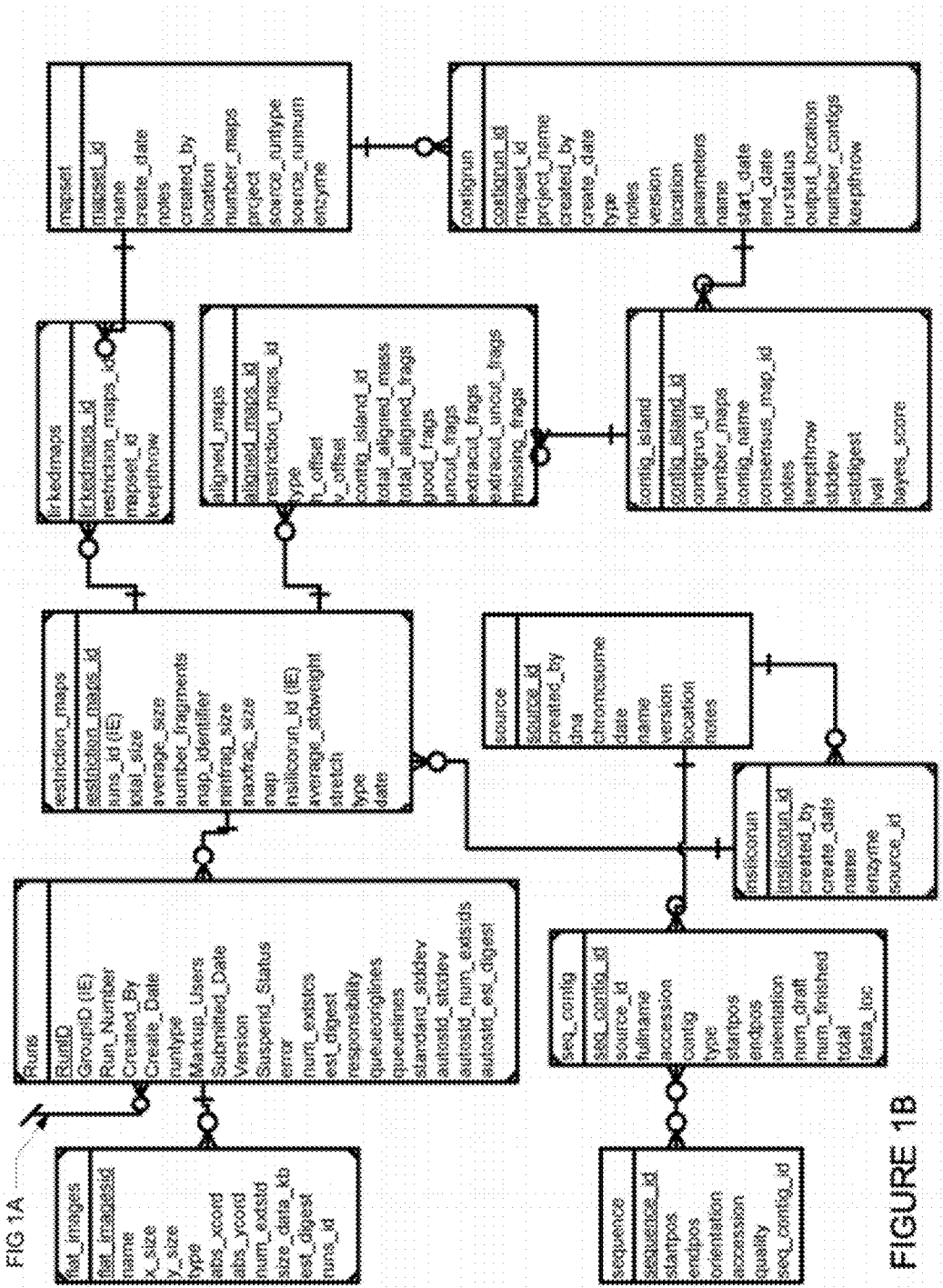

Referring to FIG. 1, in one embodiment of this disclosure, the database schema of the computer database system is depicted in an entity-relationship diagram. Each rectangular box represents an entity, the top row of which contains its name, and the multiple rows at the bottom list all the attributes of the entity. For example, one entity is Sequence, which has the name "sequence" and bear the following attributes: the identifier of the sequence (denoted as "sequence_id," which is the primary key of this entity); the starting point of the sequence (denoted as "startpos"); the end point of the sequence (denoted as "endpos"); the orientation of the sequence (denoted as "orientation"); the accession number of the sequence in a commonly referred sequence database such a GENBANK (denoted as "accession"); quality of the sequence, i.e., whether the determination of the sequence had been reliably made, with little ambiguity (denoted as "quality"); and the identifier of the contig to which the sequence belongs (denoted as "seq_contig id"). Similarly, another entity represents sequence contigs, named as "seq_contig." It is defined by a set of attributes including the accession number (denoted as "accession"), the type of the contig (denoted as "type"), its orientation (denoted as "orientation"), its starting and end points (denoted as "startpos" and "endpos," respectively), and etc.

Also usefully modeled in embodiments of database systems according to this disclosure is the entity genome (named "genome"), which has an identifier ("genome_id") as its primary key and other attributes such as its size ("genome_size"), the number of chromosomes it contains ("num chromosomes"), and whether or not it is circular ("circular"), among other things. Additionally, images are represented in the database by a number of interrelated entities, e.g., raw images (named "raw images") and flat images (named "flat images"). The primary key attribute of "raw_images" is its identifier ("raw images_id"). The other attributes include its horizontal dimension ("x_size") and vertical dimension ("y_size"), the size of the image file ("size_in_bytes"), and etc. Flat images, in an optical mapping context for example, may be derived from raw images after appropriate image processing procedures. One flat image may contain image data from a number of raw images. The primary key of "flat image" is its identifier ("flat image_id"). Other attributes are similar to those of "raw images," such as "x_size" and "y_size." However, certain attributes are unique to "flat_images" due to particular laboratory processing or analysis procedures. For instance, a flat image maybe generated from a "run" in the lab where raw images are assessed, combined, and marked up. The identifier of the procedure, or the "run," is thus recorded as one attribute of "flat_image." in this connection, another entity included in the database schema according to one embodiment is the run (named as "Runs"). it has attributes such as identifier of the run ("RunID," the primary key), its type ("runtype"), the persons performing the markup ("Markup Users'), and the error recorded ("error"), among other things.

One particularly important kind of data is restriction maps, which is also represented in the database schema in one embodiment of this disclosure, as shown in FIG. 1. This entity is named as "restriction maps." Its primary key is its identifier ("restriction_maps_id"). Other attributes include the number of fragments contained ("number_fragments"), the size of the maps ("total_size" and "average_size"), the size of the smallest fragment ("minifrag_size") and the size of the largest fragment ("maxfrag_size"), the identifier of the related run ("runs_id"), and the map ("map"), among other things. Defined as such, this entity therefore may capture all the useful information recorded in restriction maps according to embodiments described herein. Certain closely related entities—such as "linkedmaps" and "aligned_maps" as shown in FIG. 1—may also be constructed to, together with "restriction maps," enable best representation of the applicable experimental and analysis protocols and the data resulted therefrom.

As shown in FIG. 1, the entities represented by the rectangular boxes are interconnected by multiple lines, which define the relationships among the entities. One entity may link to one or more other entities. For example, the entity "restriction maps" is linked to "linked maps," "assigned maps," "runs," and "insilicorun"; and the entity "seq_contig" is connected to "sequence" and "source." A line linking two entities may be annotated according to a suitable notation system in one embodiment to define the type of relationship established, e.g., the modality and cardinality of the relationship. The generally acceptable notations in entity-relationship diagrams may be used in various embodiments. For example, the line between "aligned_map" and "restriction maps" has a perpendicular line next to the rectangular box of "restriction maps" and a circle next to the rectangular box of "aligned maps." The perpendicular line signifies that an instance of the entity "restriction maps" must exist for an instance of the entity "aligned maps" to come to being. By contrast, as signified by the circle, the presence of an instance of "restriction maps" is not conditioned upon the existence of an instance of "aligned_maps." That is, "restriction maps" may exist independently of "aligned_maps," but the reverse is not true. Such characteristic of the relationship is referred to as modality. The cardinality of this relationship is also noted in the diagram. Referring to FIG. 1, at the end of the relationship line between the entity boxes of "restriction_maps" and "aligned_maps," there are three short lines next to the circle by the box of "aligned_maps." Those multiple short lines signify that one instance of "restriction_maps" may have or correspond to multiple instances of "aligned_maps." But the reverse is not true, as reflected by the lack of such multiple short lines by the entity box of "restriction_maps."

Therefore, the entity boxes and the relationship lines may be designed and constructed to faithfully model various types of data and capture all the information generated in the studies of single macromolecules. The computer database system of this embodiment can thus support effective data management and analysis in optical mapping and in general genomics and proteomics research.

Each entity as defined in a rectangular box defines, in turn, a unique data structure representing the underlining data of interest. That is, for example, the entity "raw images," "runs," and "aligned_maps" each defines a corresponding data structure for the specific kinds of data the entity is designed to capture. These data structures may be implemented in various embodiments as different database servers are used. For example, as shown in Example I infra, the entities are implemented into a plurality of tables according to one embodiment; MYSQL is used as the database server in this example.

Separately-Operated Yet Inter-Connected Viewer and Processor

In addition to the database, as discussed in the above section, embodiments of a computer system according to this disclosure also have a viewer or a user interface that is capable of displaying different types, different configurations of data, or subsets and combinations of various kinds of data. In certain embodiments, the computer system also has a processor that is capable of processing different types of data and performing suitable analytical procedures as needed. The viewer and the processor interact with each other to enable the computer database system to effectively and efficiently respond to the user's request for data viewing and analysis. Different processing commands and instructions are formulated, some taken from the user's input whereas others implemented and maintained in the computer system of this embodiment. These instructions and commands may directly perform certain actions or accept the data or subsets of data passed and display them as desired in different views. Therefore, one architectural and mechanistic feature of the computer database system is the separate and independent—yet coordinated—operation of the viewer or the user interface and the processor. Such mechanism provides improved flexibility and efficiency in data processing and user response.

Example 2 infra shows a source code segment implementing in C++ a procedure that passes data to a command for processing according to one embodiment of this disclosure. The procedure is dubbed as a C++ class "CommandDeligate." As discussed above, the data passing implemented as such institutes modularity to the computer database system and is advantageous compared to the systems in which data is statically processed, displayed, and analyzed. After accepting the selective subsets of data, a certain command can then perform the desired operation to, for example, display the data for viewing by the user, process and/or analyze the data as predefined in the system or instructed by the user, or display the results of certain analysis steps upon completion. According to one embodiment, several types of commands are constructed in the computer system, including action commands, delegate commands, and detail commands. Action commands execute without receiving any data; they directly perform certain actions. Delegate commands (e.g., "CommandDeligate" class as described supra) enforce a specific XML data format, e.g., rowset, and hence permitting any component to attach to any view and accept data from the view without any specific knowledge on the view or the data. Detail commands, on the other hand, represent pluggable views which display some subset of data and which are capable of providing data to other commands. For example, building restriction maps for single molecules in optical mapping is part of the processing steps performed in the computer database system of this embodiment. A command is thus constructed that builds restriction maps. Similarly, as shown in Example 3 infra, a command is implemented in C++ which retrieves and aligns single molecule restriction maps according to one embodiment of this disclosure. This source code segment covers a C++ class, named "AlignGetMaps."

A multiplicity of commands may be implemented in the processor of the computer database system to enable data processing and analysis cross different data types and different technology platforms, according to various embodiments. Correspondingly, and as a result, a multiplicity of views may be enabled which can be displayed through the viewer or the user interface of the system. The display of different views may be managed and streamlined through a view manager. As shown in Example 4 infra, a procedure is implemented in C++ to manage various data views according to one embodiment of this disclosure. This source code segment covers the C++ class "ViewManager."

Figure 3:
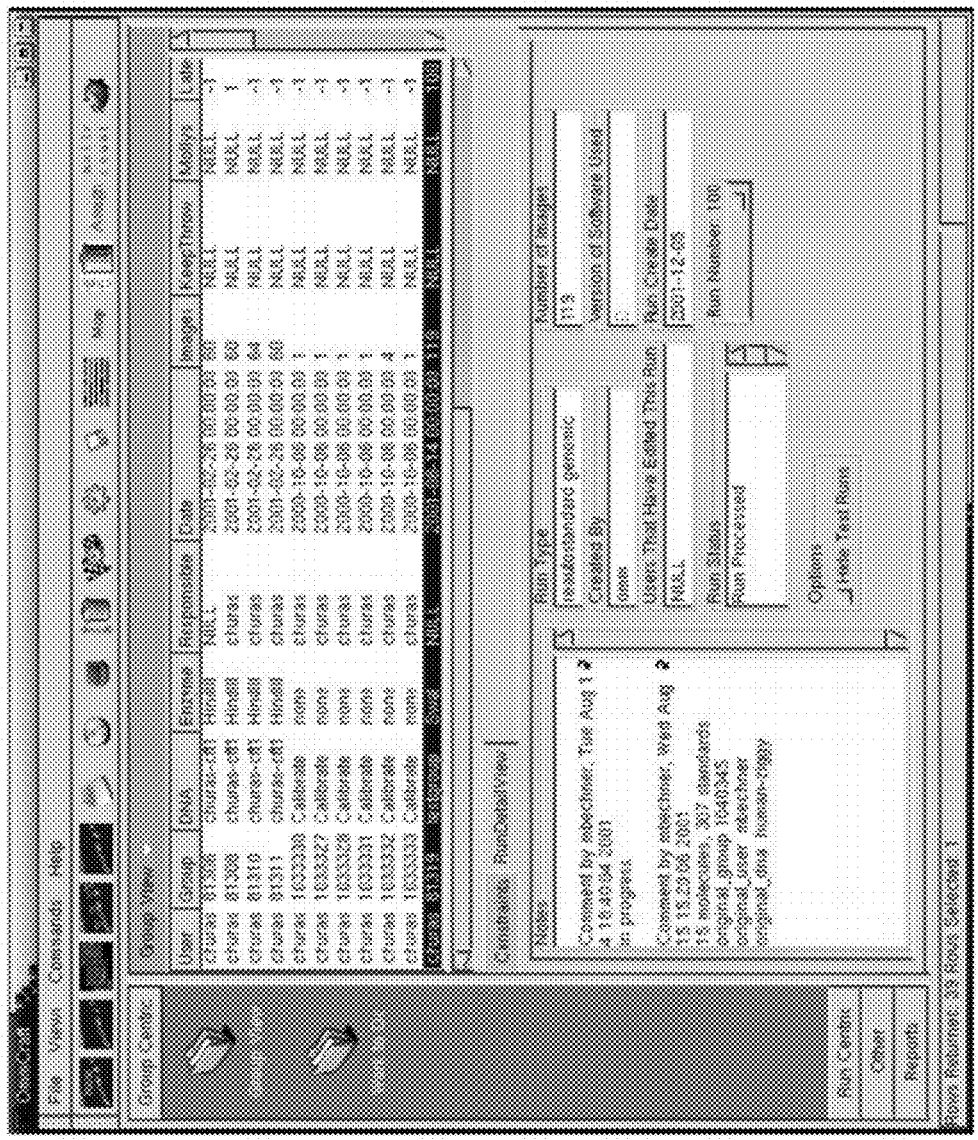
FIG. 3 is a screenshot of the user interface of the computer database system 20 according to one embodiment of this disclosure.

According to one embodiment, the view manager is a controlling object in the computer database system. It is a singleton, i.e., only one instance of this object exists at any given time, The view manger controls the various user interface components, such as the menu, the toolbar, the main window, and to act as a container for the various views. FIG. 3 presents a screenshot of the various components of the user interface (viewer) according to one embodiment of the disclosure. The toolbar includes several small icons each representing a specific command. Selecting a command icon will invoke performance of some defined action. For example, the seventh command icon from the left invokes the "ActionDiskSpace" command, displaying disk usage of the system. Similarly, another command icon will align restriction maps as implemented by "AlignGetMaps," discussed supra. On the left, the vertical panel includes view icons for the different views that have been made available, e.g., "Group View" and "Work to Do." At the bottom of this view panel are several shortcut bars, separating the different views into categories. The horizontal panel beneath the toolbar is the current view, presenting the subset of data as a corresponding view icon is selected. In the lower half of the screen, the "RunDetailView" tab provides for an implementation of the "Detail View Command," displaying additional information on the selection of data in the current view. At the left within this tab is a "Notes" textbox where further comments may be added. To the right, additional annotation boxes and graphic components are available; these include the number of images, version of the software program used, type of the run, etc. The "Constraints" tab, also in the lower half of the screen, enables additional querying on the selected subsets of data in the view.

As shown in FIG. 3, the display of various views is carefully configured and 20 managed. The view manager controls switching of views. Due to the separately operated viewer and processor, as described above, the view framework does not define the data to be displayed. It indicates only that a specific outputting format be followed if the data are to be serialized or passed to the commands for displaying through the views. For example, a particular XML format called rowset is used in this context in one embodiment of this disclosure. The interaction between the various views in the user interface (viewer) and the various commands in the processor therefore constitutes a foundation for the robust and extendable computer system according to embodiments of this disclosure.

Component Based Design Offers Added Flexibility and Efficiency

Figure 2B:
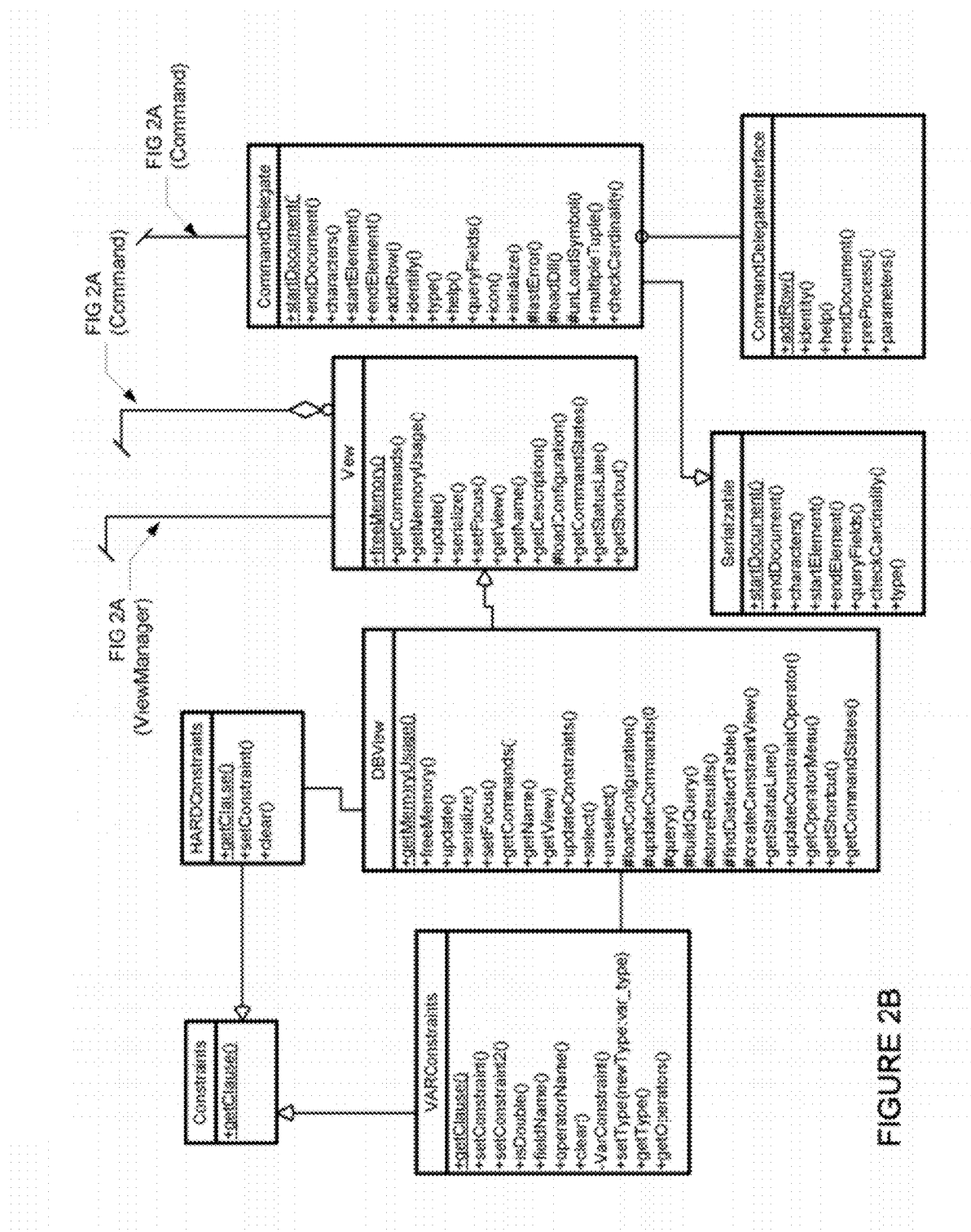

Numerous architectural and operational considerations, as discussed above, afford the flexibility and efficiency to the computer database systems of this disclosure. The component-based design enhances such feature of the system. FIG. 2 shows the logical connections among different components or objects of the computer database system according to one embodiment of this disclosure. The Unified Modeling Language (UML) is used in this diagram to depict the various components and their interrelations and interactions. The operations of the "Command," "ViewManager," "CommandDeligate," and "Constraints," for example, are laid out and defined in relation to one other.

In one embodiment, as shown in the diagram of FIG. 2 and discussed supra, a "View" defines a framework for displaying certain subset of data, it may be set by a configuration file; a "Command" defines a framework for performing certain action; and a "DBView" displays subsets of data from the database and serializes data to Commands, it contains constraints window and "DetailView" and may be configured to interact with any specific database in the system via a configuration file. Commands may be out of process (implemented using any language or platform) or in process (e.g., using C++ shared library) in various embodiments. Out-of-process commands may be installed on same or different machine whereas in-process command are deployed on the same machine. The former requires startup of separate process and the overhead of data transfer and hence is slower than the latter. An "ActionCommand" may be either in process or out of process; it is used to perform some type of action without receiving any data. A "CommandDelegate" also may be in process or out of process; it is queried as to the manageable data and data format (e.g., how many rows of data it can accept and what fields it requires) and accordingly it accepts such data passed thereto. A "DetailCommand" (also referred to as "DetailView" in the FIG. 2 diagram) may only be in process according to one embodiment. As discussed in the previous section, it is designed to present a sub-view of the current selection of data and it is capable of serialize additional data to other commands.

The choice of a flexible format, such as XML, for intermediate data passing and processing lends the system the desired adaptability. This is reflected in the interaction between the views and the commands according to embodiments of this disclosure, In one embodiment, as described in the previous section, the viewer asks every command whether they can handle the currently selected subset of data. If the command answers yes, or if the command does not require any data, the command is enabled for the user to click on and thereby execute. When a user clicks on a command that requires no data, the command simply executes and returns. Commands that requires data receive data from the view in a XML format that represents rows in a relational database (e.g., rowset). Therefore, the use of XML—or any similarly suitable data format or exchange language—keeps the separation between the viewer (the views) and the processor (the commands) clean.

The separation of business logic from the front end as such is particularly advantageous because the commands are dynamically loaded—the system is configurable—in various embodiments. By using commands as implemented, the system do not need to be concerned with the specific subsets of data being processed. Therefore, embodiments of computer database systems according to this disclosure may be applied in different contexts and with different technology platforms. Further, commands can be written in different languages besides C++, e.g., scripting languages such as Perl, according to embodiments of this disclosure. New commands can thus be made and added to the system by a user as needed. And, new views can be created on the fly to display data of the new types or from new sources as appropriate.

Various libraries and frameworks may be utilized to implement the computer database system in various embodiments. Some of the off-the-shelf software packages or publicly available programs may be adopted where appropriate to ease the development and operation of the system. For example, the GIMT toolkit (the GTK library) is used to implement the graphic user interface according to one embodiment. Further, in certain embodiment, the Common Object Request Broker Architecture (CORBA) standard is followed to implement network communications where the computer database system is deployed cross a network. This enhances the flexibility of the computer database system and makes easier and more efficient the network data transmissions within the computer database system, as well as the network transactions to and from outside sources such as outside databases. The MICO implementation of the CORBA standard is used in one embodiment of this disclosure to manage the details of routing a request from client to object, and routing the response to its destination. Other implementations and similarly appropriate data communication standard, e.g., Component Object Model (COM), may also be used according to this disclosure.

The following examples of embodiments of this disclosure are illustrative but do not limit the disclosure in any manner.

EXAMPLE 1

Database Tables Created In The Computer Database System
According To One Embodiment Using MYSQL As The Database Server

```
CREATE TABLE Counters (
    CounterID int(10) NOT NULL default '0',
    Name char(20) NOT NULL default ' ',
    Value int(10) NOT NULL default '0',
    PRIMARY KEY (CounterID)
) TYPE=MyISAM;

# These are initial values assuming a user is starting from empty database

# The only table not to have a unique ID is the Groups table since those
# ids are already generated
INSERT INTO Counters VALUES (1, 'RunID',1);
INSERT INTO Counters VALUES (2, 'QueryID',1);
INSERT INTO Counters VALUES (3, 'ProjectID',1);
INSERT INTO Counters VALUES (4, 'StandardID',1);
INSERT INTO Counters VALUES (5, 'statisticid',1);
INSERT INTO Counters VALUES (6, 'restriction_maps_id',1);
INSERT INTO Counters VALUES (7, 'mapset_id',1);
INSERT INTO Counters VALUES (8, 'linkedmaps id',1);
INSERT INTO Counters VALUES (9, 'contigrun_id',1);
INSERT INTO Counters VALUES (10, 'contig_island_id',1);
INSERT INTO Counters VALUES (11, 'aligned_maps_id',1);
INSERT INTO Counters VALUES (13, 'source_id',1);
INSERT INTO Counters VALUES (14, 'raw_images_id',1);
INSERT INTO Counters VALUES (15, 'flat_images_id',1);
INSERT INTO Counters VALUES (1000, 'FAKECOUNTER',1);

# Table structure for table 'Groups'

CREATE TABLE Groups (
    GroupID int(15) unsigned NOT NULL default'0',
    BrightID int,(10) default NULL,
    StationID int(10) unsigned default NULL,
    StandardID int(10) default NULL,
    SiteID tinyint(3) unsigned default NULL,
    Processing varchar(50) default NULL,
    Theta varchar(40) default NULL,
    Objective int(10) default NULL,
    Scale float(10,8) default NULL,
    User varchar(30) default NULL,
    Collect_Date DATETIME default NULL,
    Speed tinyint(3) unsigned default NULL,
    Gain tinyint(3) unsigned default NULL,
    Reference varchar(80) default NULL,
    Exposure int(10) unsigned default NULL,
```

EXAMPLE 1-continued

Database Tables Created In The Computer Database System
According To One Embodiment Using MYSQL As The Database Server

```
    Collect_Status
enum('COLLECTING','UNVALIDATED','VALIDATED','VALIDATED1','NOBRIGHT') default
NULL,
    Markup_Responsibility varchar(100) default NULL,
    Discrepancy varchar(100) default NULL,
    Notes text,
    Dna varchar(20) default NULL,
    Group_Loc Varchar(80) default NULL,
    Raw_Count smallint(5) unsigned default NULL,
    Archived tinyint(3) default NULL,
    Latest_Runs varchar(100) default NULL,
    Image_Collect_Time int(11) default NULL,
    station varchar(255) default NULL,
    surface varchar(100) default NULL,
    keepthrow varchar(100) default NULL,
    responsible varchar(100) default NULL,
    molecule_count varchar(100) default NULL,
    collection_id int(11) NOT NULL default '0',
    PRIMARY KEY (GroupID)
) TYPE=MyISAM;

# Table structure for table 'Runs'

CREATE TABLE Runs (
    RunID int(10) unsigned NOT NULL default '0',
    GroupID int(10) unsigned NOT NULL default '0',
    Run_Number int(10) unsigned default NULL,
    Created_By varchar(40) default ' ',
    Create_Date date default '0000-00-00',
    runtype varchar(50) default NULL,
    Markup_Users Varchar(80) default ' ',
    Submitted_Date int(10) default NULL,
    Version varchar(30) default ' ',
    Suspend_Status varchar(30) default ' ',
    error varchar(255) default NULL,
    num_extstds int(11) default NULL,
    est_digest float(10,2) default NULL,
    responsibility varchar(255) default NULL,
    queueoriglines int(11) default NULL,
    queuelines int(11) default NULL,
    standard_stddev float(8,2) default NULL,
    autostd_stddev float(4,2) default NULL,
    autostd_num_extstds int(11) default NULL,
    autostd_est_digest float(4,2) default NULL,
    PRIMARY KEY (RunID),
    KEY GroupID(GroupID)
) TYPE=MyISAM;

# Table structure for table 'Standards'

CREATE TABLE Standards (
    StandardID int(10) unsigned NOT NULL default '0',
    Standard char(25) default ' ',
    Enzyme char(25) default ' ',
    PRIMARY KEY (StandardID)
) TYPE=MyISAM;
# needed for the unknown case
INSERT INTO Standards (StandardID,Standard,Enzyme)
VALUES(0,"unknown","unknown");

# Table structure for table 'aligned_maps'

CREATE TABLE aligned_maps (
    aligned_maps_id varchar(40) NOT NULL default ' ',
    restriction_maps_id int(11) default NULL,
    type varchar(50) default NULL,
    h_offset smallint(6) default NULL,
    v_offset smallint(6) default NULL,
    contig_island_id varchar(40) default NULL,
    total_aligned_mass float NOT NULL default '0',
    total_aligned_frags int(11) NOT NULL default '0',
    good_frags int(11) NOT NULL default '0',
    uncut_frags mediumint(8) unsigned NOT NULL default '0',
    extracut_frags mediumint(8) unsigned NOT NULL default '0',
    extracut_uncut_frags mediumint(8) unsigned NOT NULL default '0',
```

EXAMPLE 1-continued

Database Tables Created In The Computer Database System
According To One Embodiment Using MYSQL As The Database Server

```
    missing_frags mediumint(8) unsigned NOT NULL default '0',
    PRIMARY KEY (aligned_maps_id)
) TYPE=MyISAM;

# Table structure for table 'collection'

CREATE TABLE collection (
    id int(11) NOT NULL default '0',
    created_by char(50) NOT NULL default '0',
    create_date datetime NOT NULL default '0000-00-00 00:00:00',
    project_id int(11) NOT NULL default '0',
    station char(50) NOT NULL default ' ',
    standard_id int(11) NOT NULL default '0',
    PRIMARY KEY (id)
) TYPE=MyISAM;

# Table structure for table 'contig_island'

CREATE TABLE contig_island (
    contig_island_id varchar(40) NOT NULL default ' ',
    contigrun_id varchar(40) default NULL,
    consensus_map_id int(11) default NULL,
    number_maps int(11) default NULL,
    stddev float(8,2) default NULL,
    estdigest float(8,2) default NULL,
    contig_name varchar(64) default NULL,
    keepthrow varchar(100) default NULL,
    tval float(8,4) NOT NULL default '0.0000',
    bayes_score float(8,4) NOT NULL default '0.0000',
    PRIMARY KEY (contig_island_id),
    KEY contigrun_id_index (contigrun_id)
) TYPE=MyISAM;

# Table structure for table 'contigrun'

CREATE TABLE contigrun (
    contigrun_id varchar(40) NOT NULL default ' ',
    mapset_id varchar(40) default NULL,
    project_name varchar(64) default NULL,
    user varchar(255) default NULL,
    create_date datetime default NULL,
    type varchar(50) default NULL,
    notes text,
    version varchar(25) default NULL,
    location varchar(255) default NULL,
    parameters text,
    name varchar(255) default NULL,
    start_date datetime default NULL,
    end_date datetime default NULL,
    runstatus varchar(50) default NULL,
    output_location varchar(255) default NULL,
    number_contigs int(11) default NULL,
    keepthrow varchar(100) default NULL,
    host varchar(50) NOT NULL default ' ',
    seedmapset_id varchar(40) NOT NULL default ' ',
    lower_s float NOT NULL default '0',
    capital_s float NOT NULL default '0',
    capital_sl float NOT NULL default '0',
    capital_sm float NOT NULL default '0',
    capital_d float NOT NULL default '0',
    capital_f float NOT NULL default '0',
    capital_pm float NOT NULL default '0',
    capital_cn float NOT NULL default '0',
    capital_g float NOT NULL default '0',
    capital_v float NOT NULL default '0',
    capital_t float NOT NULL default '0',
    capital_t_str varchar(100) NOT NULL default ' ',
    capital_m int(11) NOT NULL default '0';
    capital_c float NOT NULL default '0',
    capital_cs float NOT NULL default '0',
    capital_b tinyint(4) NOT NULL default '0',
    capital_bsiz float NOT NULL default '0',
    capital_bridge int(11) NOT NULL default '0',
    capital_bend int(11) NOT NULL default '0',
    capital_bminend int(11) NOT NULL default '0',
    capital_blink int(11) NOT NULL default '0',
    capital_g tinyint(4) NOT NULL default '0',
```

EXAMPLE 1-continued

Database Tables Created In The Computer Database System
According To One Embodiment Using MYSQL As The Database Server

```
    nohash tinyint(4) NOT NULL default '0',
    lower_q varchar(50) NOT NULL default ' ',
    capital_hq float NOT NULL default '0',
    capital_he float NOT NULL default '0',
    capital_hs float NOT NULL default '0',
    capital_ha float NOT NULL default '0',
    mapordered tinyint(4) NOT NULL default '0',
    lower_p varchar(50) NOT NULL default ' ',
    r_min float NOT NULL default '0',
    r_max float NOT NULL default '0',
    lower_partial text NOT NULL,
    csort varchar(100) NOT NULL default ' ',
    csortm varchar(100) NOT NULL default ' ',
    msort tinyint(4) NOT NULL default '0',
    nosort tinyint(4) NOT NULL default '0',
    qsort tinyint(4) NOT NULL default '0',
    cfirst int(11) NOT NULL default '0',
    cfirstw float NOT NULL default '0',
    cfirstwe float NOT NULL default '0',
    mblast int(11) NOT NULL default '0',
    mblastw float NOT NULL default '0',
    mblastfalse tinyint(4) NOT NULL default '0',
    mrand int(11) NOT NULL default '0',
    opt int(11) NOT NULL default '0',
    optm int(11) NOT NULL default,'0',
    lower_a int(11) NOT NULL default '0',
    lower_b int(11) NOT NULL default '0',
    lower_l float NOT NULL default '0',
    capital_w float NOT NULL default '0',
    capital_l float NOT NULL default '0',
    hashmin tinyint(4) NOT NULL default '0',
    minfrag float NOT NULL default '0',
    minmol float NOT NULL default '0',
    autoseed float NOT NULL default '0',
    capital_e int(11) NOT NULL default '0 ',
    capital_a int(11) NOT NULL default '0',
    lower_e float NOT NULL default '0',
    lower_q_k int(11) NOT NULL default '0',
    PRIMARY KEY (contigrun_id),
    KEY mapset_id_index (mapset_id)
) TYPE=MyISAM;

# Table structure for table 'enzyme'

CREATE TABLE enzyme (
    id int(11) NOT NULL auto_increment,
    name char(50) NOT NULL default ' ',
    PRIMARY KEY (id),
    UNIQUE KEY name (name)
) TYPE=MyISAM;

# Table structure for table 'enzymes'

CREATE TABLE enzymes (
    enzymesid int(11) NOT NULL default '0',
    StandardID int(10) unsigned NOT NULL default '0',
    segment_lengths float(10,8) default NULL,
    PRIMARY KEY (enzymesid),
    KEY StandardID(StandardID)
) TYPE=MyISAM;

# Table structure for table 'flat_images'

CREATE TABLE flat_images (
    flat_images_id int(11) NOT NULL default '0',
    name varchar(255) default NULL,
    x_size int(11) default NULL,
    y_size int(11) default NULL,
    type varchar(25) default NULL,
    num_extstd int(11) default NULL,
    abs_xcord int(11) default NULL,
    abs_ycord int(11) default NULL,
```

EXAMPLE 1-continued

Database Tables Created In The Computer Database System
According To One Embodiment Using MYSQL As The Database Server

```
    size_in_bytes int(11) default NULL,
    runs_id int(11) default NULL,
    PRIMARY KEY (flat_images_id)
) TYPE=MyISAM:

# Table structure for table 'genome'

CREATE TABLE genome (
    genome_id char(40) NOT NULL default ' ',
    dna char(50) NOT NULL default ' ',
    leader char(50) default NULL,
    genome_size int(11) default NULL,
    num_chromosomes int(11) default NULL,
    circular char(2) default NULL;
    created_by char(50) default NULL,
    create_date date default NULL,
    PRIMARY KEY (genome_id),
    UNIQUE KEY dna (dna)
) TYPE=MyISAM;

# Table structure for table 'groupset'

CREATE TABLE groupset (
    id int(11) NOT NULL auto_increment,
    name varchar(255) NOT NULL default ' ',
    create_date date NOT NULL default '0000-00-00',
    created_by varchar(255) NOT NULL default ' ',
    enzyme varchar(25) NOT NULL default ' ',
    notes text NOT NULL,
    PRIMARY KEY (id)
) TYPE=MyISAM;

# Table structure for table 'insilicorun'

CREATE TABLE insilicorun (
    insilicorun_id int(11) NOT NULL default '0',
    user varchar(255) default NULL,
    create_date date default NULL,
    name varchar(255) default NULL,
    enzyme varchar(255) default NULL,
    source_id int(11) default NULL,
    PRIMARY KEY (insilicorun_id)
) TYPE=MyISAM;

# Table structure for table 'linkedgroups'

CREATE TABLE linkedgroups (
    id int(11) NOT NULL auto_increment,
    groups_id int(11) NOT NULL default '0',
    groupset_id int(11) NOT NULL default '0',
    PRIMARY KEY (id),
    KEY groupidx (groups_id),
    KEY gsetidx (groupset_id)
) TYPE=MyISAM;

# Table structure for table 'linkedmaps'

CREATE TABLE linkedmaps (
    linkedmaps_id varchar(40) NOT NULL default ' ',
    restriction_maps_id int(11) default NULL,
    mapset_id varchar(40) default NULL,
    keepthrow char(2) default 'T',
    PRIMARY KEY (linkedmaps_id),
    KEY restriction_maps_id_index (restriction_maps_id),
    KEY mapset_id_index (Mapset_id)
) TYPE=MyISAM;

# Table structure for table 'linkedseedmaps'

CREATE TABLE linkedseedmaps (
    id varchar(40) NOT NULL default ' ',
    restriction_maps_id int(11) NOT NULL default '0',
```

EXAMPLE 1-continued

Database Tables Created In The Computer Database System
According To One Embodiment Using MYSQL As The Database Server

```
   contigrun_id varchar(40) NOT NULL default ' ',
   PRIMARY KEY (id)
) TYPE=MyISAM;

# Table structure for table 'mapset'

CREATE TABLE mapset (
   mapset_id varchar(40) NOT NULL default ' ',
   name varchar(255) default NULL,
   create_date date default NULL,
   notes text,
   created_by varchar(255) default NULL,
   location varchar(255) default NULL,
   number_maps int(11) default NULL,
   project varchar(100) default NULL,
   source_runtype varchar(100) default NULL,
   source_runnum varchar(20) default NULL,
   enzyme varchar(25) default NULL,
   PRIMARY KEY (mapset_id)
) TYPE=myISAM;
#default 0 id mapset in event contigs exist where there isnt a mapset

INSERT INTO mapset VALUES ('0','nomapset','1900-01-
11',NULL,NULL,'0',NULL,NULL,NULL,NULL,NULL);

# Table structure for table 'project'

CREATE TABLE project (
   id int(11) NOT NULL auto_increment,
   leader char(100) NOT NULL default ' ',
   min_map_size int(11) NOT NULL default '0',
   expected_map_size int(11) NOT NULL default '0',
   expected_avg_frag int(11) NOT NULL default '0',
   create_date date NOT NULL default '0000-00-00',
   created_by char(50) NOT NULL default ' ',
   desired_coverage int(11) NOT NULL default '0',
   genome_id int(11) NOT NULL default '0',
   name char(50) NOT NULL default ' ',
   enzyme_id int(11) NOT NULL default '0',
   PRIMARY KEY (id)
) TYPE=MyISAM;

# Table structure for table 'raw images'

CREATE TABLE raw images (
   raw_images_id int(11) NOT NULL default '0',
   name varchar(255) default NULL,
   x_size int(11) default NULL,
   y_size int(11) default NULL,
   type varchar(25) default NULL,
   size_in_bytes int(11) default NULL,
   groups_id int(11) default NULL,
   PRIMARY KEY (raw_images_id)
) TYPE=MyISAM;

# Table structure for table 'restriction maps'

CREATE TABLE restriction_maps (
   restriction_maps_id int(11) NOT NULL default '0',
   runs_id int (11) maps_default NULL,
   insilicorun_id int(11) default '0',
   map_identifier varchar(255) default NULL,
   number_fragments int(11) default NULL,
   minfrag_size float(10,2) default NULL,
   maxfrag_size float(10,2) default NULL,
   average_size float(10,2) default NULL,
   total_size float(10,2) default NULL,
   map text,
   average_stdweight float(5,3) default NULL,
   stretch float(6,4) default NULL,
   type varchar(5) default NULL,
   date datetime default NULL,
   PRIMARY KEY (restriction_maps_id),
```

EXAMPLE 1-continued

Database Tables Created In The Computer Database System
According To One Embodiment Using MYSQL As The Database Server

```
    KEY runindex(runs_id),
    KEY map_identifier_index(map_identifier),
    KEY insilicorun_id_index(insilicorun_id)
) TYPE=MyISAM;

# Table structure for table 'seq_contig'

CREATE TABLE seq_contig (
    seq_contig_id int(11) NOT NULL default '0',
    source_id int(11) default NULL,
    fullname varchar(255) default NULL,
    accession varchar(255) default NULL,
    contig varchar(255) default NULL,
    type varchar(10) default NULL,
    startpos int(11) default NULL,
    endpos int(11) default NULL,
    orientation varchar(8) default NULL,
    num_draft int(11) default NULL,
    num_finished int(11) default NULL,
    total int(11) default NULL,
    fasta_loc varchar(255) NOT NULL default ' ';
    PRIMARY KEY (seq_contig_id)
) TYPE=MyISAM;

# Table structure for table 'seq_om_alignment'

CREATE TABLE seq_om alignment (
    id int(11) NOT NULL auto_increment,
    contigrun_id char(40) NOT NULL default ' ',
    seq_contig_id int(11) NOT NULL default '0',
    sequence_map_id int(11) NOT NULL default '0',
    optical_map_id int(11) NOT NULL default '0',
    seq_start int(11) NOT NULL default '0',
    seq_end int(11) NOT NULL default '0',
    grade char(20) NOT NULL default ' ',
    opmapOverlapMass float(10,4) NOT NULL default '0.0000',
    opmapOverlapPercent float(10,4) NOT NULL default '0.0000',
    opmapNumAlignFrags int(11) NOT NULL default '0',
    seqmapNumAlignFrags int(11) NOT NULL default '0',
    totalSizingError float(10,4) NOT NULL default '0.0000',
    meanSizingError float(10,4) NOT NULL default '0.0000',
    digestRate float(10,4) NOT NULL default '0.0000',
    falseCutRatePerMB float(10,4) NOT NULL default '0.0000',
    numMissedCuts int(11) NOT NULL default '0',
    numFalseCuts int(11) NOT NULL default '0',
    numMissingFrags int(11) NOT NULL default '0',
    numMissingFrags1to5kb int(11) NOT NULL default '0',
    numMissingFragsOver5kb int(11) NOT NULL default '0',
    meanMissingMass float(10,4) NOT NULL default '0.0000',
    maxMissingMass float(10,4) NOT NULL default '0.0000',
    numExtraFrags int(11) NOT NULL default '0',
    meanExtraFragMass float(10,4) NOT NULL default '0.0000',
    maxExtraFragMass float(10,4) NOT NULL default '0.0000',
    tval float(8,4) NOT NULL default '0.0000',
    bayes_score float(8,4) NOT NULL default '0.0000',
    keepflag tinyint(4) NOT NULL default '0',
    PRIMARY KEY (id),
    KEY crunidx (contigrun_id),
    KEY s_con_idx (seq_contig_id),
    KEY seq_map_idx (sequence_map_id),
    KEY op_map_idx (optical_map_id)
) TYPE=MyISAM;

# Table structure for table 'sequence'

CREATE TABLE sequence (
    sequence_id varchar(40) NOT NULL default ' ',
    startpos int(11) default NULL,
    endpos int(11) default NULL,
    orientation char(2) default NULL,
    accession varchar(50) default NULL,
    quality char(2) default NULL,
```

EXAMPLE 1-continued

Database Tables Created In The Computer Database System
According To One Embodiment Using MYSQL As The Database Server

```
   seq_contig_id int(11) default NULL,
   PRIMARY KEY (sequence_id)
) TYPE=MyISAM;

# Table structure for table 'source'

CREATE TABLE source (
   source_id int(11) NOT NULL default '0',
   user varchar(255) default NULL,
   dna varchar(255) default NULL,
   chromosome varchar(255) default NULL,
   date date default NULL,
   name varchar(255) default NULL,
   version tinyint(4) default NULL,
   location varchar(255) default NULL,
   notes text,
   PRIMARY KEY (source_id)
) TYPE=MyISAM;

# Table structure for table 'sourcedb'

CREATE TABLE sourcedb (
   sourcedb_id int(11) NOT NULL auto_increment,
   login varchar(100) default NULL,
   type varchar(50) default NULL,
   create_date datetime default NULL,
   file varchar(255) default NULL,
   revision varchar(50) default NULL,
   notes text,
   os varchar(50) default NULL,
   PRIMARY KEY (sourcedb_id)
) TYPE=MyISAM;

# Table structure for table 'staff'

CREATE TABLE staff (
   staff_id char(40) NOT NULL default ' ',
   fullname char(255) default NULL,
   login char(100) NOT NULL default ' ',
   email char(255) default NULL,
   PRIMARY KEY (staff_id),
   UNIQUE KEY login (login)
) TYPE=MyISAM;

# Table structure for table 'standard'

CREATE TABLE standard (
   id int(11) NOT NULL auto_increment,
   standard char(100) NOT NULL default ' ',
   enzyme_id int(11) NOT NULL default '0',
   cuts char(255) NOT NULL default ' ',
   created_by char(50) NOT NULL default ' ',
   create_date date NOT NULL default '000000-00',
   PRIMARY KEY (id)
) TYPE=MyISAM;

# Table structure for table 'statistics'

CREATE TABLE statistics (
   statisticid int(11) NOT NULL default '0',
   program varchar(100) default NULL,
   query text,
   times_called int(11) default NULL,
   date datetime default NULL,
   user varchar(255) default NULL,
   PRIMARY KEY (statisticid)
) TYPE=MyISAM;
```

EXAMPLE 2

A Procedure In A Computer Database System According to One Embodiment Of This Disclosure For Passing Data To A Command For Processing Implemented Using C++

```cpp
#include <sax2/Attributes.hpp>
#include <util/XMLUniDefs.hpp>
#include <sax2/ContentHandler.hpp>
#include <sax/ErrorHandler.hpp>
#include <sax/SAXParseException.hpp>
#include <dlfcn.h>
#include <iostream>
#include <vector>
#include <string>
#include <fstream.h>
#include <sys/stat.h>
#include <unistd.h>
#include <typeinfo>
#include <stdlib.h>
#include "libomm/CommandException.hpp"
#include "CommandDelegate.hpp"
CommandDelegate::CommandDelegate(string *commandName,CORBA::ORB_ptr orb)
    : mp_pInterface(NULL), mp_pVoidHandle(NULL), mp_State(UNDEF), mp_pOrb(orb),
      mp_Min(-1),mp_Max(-1)
{
    //clear the vectors just to be safe
    mp_FieldNames.clear( );
    mp_SingleRow.clear( );
    mp_RequiredFields.clear( );
    mp_pCommandName = new string(*commandName);
    //mp_Min=-1;
    //mp_Max=-1;
}
CommandDelegate::~CommandDelegate( )
{
    emptyFieldNames( );
    emptySingleRow( );
    for (int i = 0; i < (int)mp_RequiredFields.size( ); i++)
        delete mp_RequiredFields[i];
    mp_RequiredFields.clear( );
    unLoadSymbol( );
    delete mp_pCommandName;
    return;
}
string *CommandDelegate::identity( )
{
    //set the name to be anything right of last / in commandname or whole
    //command name if no slash exists
    char *tempPtr = NULL;
    char *periodPtr = NULL;
    string *finalString = NULL;
    char *tempString = new char[strlen(mp_pCommandName->c_str( ))+1];
    strcpy(tempString,mp_pCommandName->c_str( ));
    tempPtr = rindex(tempString,'/');
    if (tempPtr != NULL) {
        tempPtr++;
        periodPtr = rindex(tempPtr,'.');
        if (periodPtr != NULL)
            "periodPtr = '\0';
        finalString = new string(tempPtr);
        delete tempString;
        return finalString;
    }
    periodPtr = rindex(tempPtr,'.');
    if (periodPtr != NULL) {
        *periodPtr = '\0';
        finalString = new string(tempPtr);
    }
    else {
        finalString = new string(*mp_pCommandName);
    }
    delete tempString;
    return finalString;
}
int CommandDelegate::type( )
{
    return 2; //default type for commanddelegate.
}
string *CommandDelegate::help( )
{
    //for now just return name of command.
    /** @todo need to actually cache and call help method of command */
```

EXAMPLE 2-continued

A Procedure In A Computer Database System According to One Embodiment Of This Disclosure For Passing Data To A Command For Processing Implemented Using C++

```
   char *tempPtr = NULL;
   string *myPtr = NULL;
   tempPtr = rindex(mp_pCommandName->c_str( ),'/');
   if (tempPtr != NULL) {
      tempPtr++;
      myPtr=new string(tempPtr);
      return myPtr;
   }
   myPtr = new string(*mp_pCommandName);
   return myPtr;
}
void CommandDelegate::startDocument( )
{
   //calls the preprocess method of command
      mp_State = UNDEF;
      if (mp_pInterface == NULL)
         Initialize( );
      if (mp_pInterface == NULL)
      {
          string errormsg = string("Error Object: " + *mp_pCommandName + " is
Null.");
          throw CommandException(errormsg.c_str( ));
      }
      if (CORBA::is_nil(mp_pInterface)){
          string errormsg = string("Error Object: " + *mp_pCommandName + " is
NULL.");
          throw CommandException(errormsg.c_str( ));
      }
      try {
          mp_pInterface->preProcess( );
      }
      catch (CORBA::Exception &ex) {
          string errormsg = string("Error Object: " + *mp_pCommandName + " is
inaccessible.");
          throw CommandException(errormsg.c_str( ));
      }
      return;
}
void CommandDelegate::endDocument( )
{
   //calls enddocument method of command
      //at the end of a document clear the two vectors and unset the state
      mp_State = UNDEF;
      emptySingleRow( );
      emptyFieldNames( );
      if (mp_pInterface == NULL)
      {
          string errormsg = string("Error Object: " + *mp_pCommandName + "is
NULL.");
          throw CommandException(errormsg.c_str( ).);
      }
      if (CORBA::is_nil(mp_pInterface)){
          string errormsg = string("Error Object: " + *mp_pCommandName + " is
NULL.");
          throw CommandException(errormsg.c_str( ));
      }
      try {
          mp_pInterface->endDocument( );
      }
      catch (CORBA::Exception & ex) {
          string errormsg = string("Error Object: " + *mp_pCommandName + " is
inaccessible.");
          throw CommandException(errormsg.c_str( ));
      }
      unLoadSymbol( );
      return;
}
void CommandDelegate::characters(const XMLCh *chars, unsigned int length)
{
   string *temp;
   char *tempptr;
   //if we aren't in any fields we care about just return
   if (mp_State == UNDEF) return;
   //if the chars variable is null just return
   if (chars == NULL) return;
   //allocate a new string to hold the contents of chars
   //a pointer to this allocated memory will be put in the vectors
```

EXAMPLE 2-continued

A Procedure In A Computer Database System According to One Embodiment Of
This Disclosure For Passing Data To A Command For Processing Implemented Using C++

```
    tempptr = XMLString::transcode(chars);
    temp = new string(tempptr);
    delete tempptr;
    //if we have we have a mp_FieldNames or FIELD state store the
    //data from chars to the appropriate vector
    if (mp_State == FIELDNAMES) {
        mp_FieldNames.push_back(temp);
    }
    else if (mp_State == FIELD) {
        mp_SingleRow.push_back(temp);
    }
    else {
        delete temp; //just in case it isn't one of the fields we are
    }            //interested in free the memory
    return;
}
//---------------------------------------
void CommandDelegate::startElement(const XMLCh *uri,
                                   const XML* const localname,
                                   const XMLCh* const qname,
                                   const class Attributes &a)
{
    string *temp;
    char *tempptr;
    //if localname is null just return
    if (localname == NULL) return;
    //store contents of localname in string temp
    tempptr = XMLString::transcode(localname);
    temp = new string(tempptr);
    delete tempptr;
    //set the state correctly for characters function which will
    //only add data to the vectors if its in the right state
    //if neither field matches set state to UNDEF
    if (*temp == FIELDNAME_TAG) {
        mp_State = FIELDNAMES;
    }
    else if (*temp == FIELD_TAG) {
        mp_State = FIELD;
    }
    else {
        mp_State = UNDEF;
    }
    delete temp;
    return;
}
//---------------------------------------
voidCommandDelegate::endElement(constXMLCh *const uri, const XMLCh *const
                   localname, const XMLCh *const qname)
{
    string *temp;
    char *tempptr;
    int vectorSize = 0;
    //if localname is null just return
    if (localname == NULL) return;
    //store the contents of localname in temp
    tempptr = XMLString::transcode(localname);
    temp = new string(tempptr);
    delete tempptr;
    // if the end tag is a ROWSET_TAG call the process function of the plugin
    if (*temp == ROWSET_TAG) {
        // make sure the sizes of the fieldnames and single row match
        if (mp_FieldNames.size( ) == mp_SingleRow.size( )) {
            vectorSize = (int)mp_FieldNames.size( );
            //THIS IS WHERE THE ADDROW IS CALLED
            StringSeq fields,singleRow;
            fields.length((CORBA::ULong)vectorSize);
            singleRow.length((CORBA::ULong)vectorSize)
            //** @todo need to add exception if object is not available */
            for (int i =0; i < vectorSize; i++) {
            fields[i] = (const char *)mp_FieldNames[i]->c_str( );
            singleRow[i] = (const char *)mp_SingleRow[i]->c_str( );
            }
            if (mp_pInterface == NULL) {
                emptySingleRow( );
                emptyFieldNames( );
            string errormsg = string("Error Object: "+ *mp_pCommandName
                        + " is NULL.");
```

EXAMPLE 2-continued

A Procedure In A Computer Database System According to One Embodiment Of
This Disclosure For Passing Data To A Command For Processing Implemented Using C++

```
        throw CommandException(errormsg.c_str( ));
      }
      if (CORBA::is_nil(mp_pInterface)) {
        emptySingleRow( );
           emptyFieldNames( );
        stringerrormsg = string("Error Object: "+ *mp_pCommandName
                       + " is NULL.");
        throw CommandException(errormsg.c_str( ));
      }
      try {
      mp_pInterface->addRow(fields,singleRow);
      }
      catch (CORBA::Exception &ex) {
      string errormsg = string("Error calling addrow on Object: "+
                    *mp_pCommandName+ " raised error.");
        emptySingleRow( );
        emptyFieldNames( );
        throw CommandException(errormsg.c_str( ));
      }
    }
    else {
      cout <<"single row size: "<<mp_SingleRow.size( );
      cout <<" fields size: "<<mp_FieldNames.size( )<<end1;
      for (int xx = 0; xx < (int)mp_SingleRow.size( ); xx++)
        cout <<"Rows"<<*mp_SingleRow[xx]<<end1;
      for (int xx = 0; xx < (int)mp_FieldNames.size( ); xx++)
        cout <<"fields"<<*mp_FieldNames[xx]<<end1;
      emptySingleRow( );
      emptyFieldNames( );
        string errormsg = string("Error Vector Sizes Don't match.");
        throw CommandException(errormsg.c_str( ));
    }
    //delete contents of the data fields
    emptySingleRow( );
  }
  else if (*temp == FIELDS_TAG) {
    delete temp;
    mp_State = UNDEF;
    return;
  }
  mp_State = UNDEF;
  delete temp;
  return;
}
//-----------------------------------
vector <string *> *CommandDelegate::queryFields( )
{
  //** if the fields have already been obtained then simply copy and return
   * a new vector with the fields if not connect to command and obtain
   * fields
   */
  vector <string*> * tempVector = NULL;
  if (!mp_RequiredFields.empty( )){
    tempVector = new vector<string *>;
    for (int i = 0; i < (int)mp_RequiredFields.size( ); i++){
      tempVector->push_back(new string(*mp_RequiredFields[i]));
    }
    return tempVector;
  }
    Initialize( );
    StringSeq *temp;
    if (mp_pInterface == NULL) {
       string errormsg = string("Error Object: " + *mp_pCommandName
                       + " is NULL.");
       throw CommandException(errormsg.c_str( ));
    }
    if (CORBA::is_nil(mp_pInterface)) {
       string errormsg = string("Error Object: " + *mp_pCommandName + " is
NULL.");
       throw CommandException(errormsg.c_str( ));
    }
    try {
      temp = mp_pInterface->queryFields( );
    }
    catch (CORBA::Exception &ex) {
       string errormsg = string("Error calling queryfields on Object: "+
                    *mp_pCommandName+ " raised exception.");
```

EXAMPLE 2-continued

A Procedure In A Computer Database System According to One Embodiment Of
This Disclosure For Passing Data To A Command For Processing Implemented Using C++

```
        throw CommandException(errormsg.c_str( ));
    }
    if (temp ==NULL)
        return NULL;
    /** @todo need to throw exceptions here */
    /** @todo need to fix possible memory leak here */
    need to convert sequence to a vector of string pointers
    mp_RequiredFields.clear( );
    vector <string *> *theList = new vector<string *>;
    for (int i = 0; i<(int)temp->length( ); i++) {
        theList->push_back(new string(temp->operator[ ](i).in( )));
        mp_RequiredFields.push_back(new string(temp->operator[ ](i).in( )));
        CORBA::string_free((char *)temp->operator[ ](i).in( ));
    }
    CORBA::string_free((char *)temp);
    return theList;
}
//----------------------------------------------------
bool CommandDelegate::checkCardinality(int tuples)
{
    bool deleteSymbol = FALSE;
    int min,max;
    in (mp_Min == -1)
    {
        if (mp_pInterface == NULL)
        {
            deleteSymbol = TRUE;
            Initialize( );
        }
        if (mp_pInterface == NULL)
        {
            string errormsg = string("Error Object: "+
                            *mp_pCommandName+ "is NULL.");
            throw CommandException(errormsg.c_str( ));
        }
        if (CORBA::is_nil(mp_pInterface(( {
            string errormsg = string("Error Object: "+
                            *mp_pCommandName+ " is NULL.");
            throw CommandException(errormsg.c_str( ));
        }
        try
        {
            min = mp_pInterface->getMin( );
            max = mp_pInterface->getMax( );
        }
        catch (CORBA::Exception &ex)
        {
            string errormsg = string("Error calling getmin/max on Object: "+
                            *mp_pCommandName+ " raised exception.");
            throw CommandException(errormsg.c_str( ));
        }
        if (deleteSymbol == TRUE)
            unLoadSymbol( );
        mp_Min = min;
        mp_Max = max;
    }
    if (tuples >= mp_Min && tuples <= mp_Max)
        return TRUE;
    return FALSE;
}
void CommandDelegate::emptySingleRow( )
{
  //loop thru the vector and delete the memory the string pointers are
  //pointing to
    if (mp_SingleRow.empty( ) == TRUE)
        return;
  for (int x = 0; x < (int)mp_SingleRow.size( ); x++)
     delete mp_SingleRow[x];
  mp_SingleRow.clear( );
  return;
}
//---------------------------------------
void CommandDelegate::emptyFieldNames( )
}
    //loop thru the vector and delete the memory the string pointers are
    //pointing to
       if (mp_FieldNames.empty( ) == TRUE)
```

EXAMPLE 2-continued

A Procedure In A Computer Database System According to One Embodiment Of
This Disclosure For Passing Data To A Command For Processing Implemented Using C++

```
      return;
   for (int x = 0; x < (int)mp_FieldNames.size( ); x++)
      delete mp_FieldNames[x];
   mp_FieldNames.clear( );
   return;
}
//---------------------------------------
void CommandDelegate::ignorableWhitespace(const XMLCh *charData,
                                          unsigned int spaces)
{
    return;
}
//-------------------------------------------------------------
void CommandDelegate::warning(const SAXParseException &e)
{
   char errormsg(BUFSIZ);
   char *tempptr = NULL;
   char *tmpptr = NULL;
   tempptr = XMLString::transcode(e.getSystemId( ));
   tempptr = XMLString::transcode(e.getMessage( ));
   snprintf(errormsg,BUFSIZ,"\nWarning at file %s, line %d, char %d\n Message:
%s\n",tempptr,e.getLineNumber( ),e.getColumnNumber( ),tmpptr);
   delete tempptr;
   delete tmpptr;
   throw CommandException(errormsg);
}
//-------------------------------------------------------------
void CommandDelegate::error(const SAXParseException &e)
{
   char errormsg[BUFSIZ];
   char *tempptr = NULL;
   char *tmpptr = NULL;
   tempptr = XMLString::transcode(e.getSystemId( ));
   tmpptr = XMLString::transcode(e.getMessage( ));
   snprintf(errormsg,BUFSIZ,"\nError at file % s, line %d, char %d\n Message:
%s\n", tempptr,e.getLineNumber( ),e.getColumnNumber( ),tmpptr);
   delete tmpptr;
   delete tempptr;
   throw CommandException(errormsg);
}
//-------------------------------------------------------------
void CommandDelegate::fatalError(const SAXParseException &e)
{
   char errormsg[BUFSIZ];
   char *tmpptr = NULL;
   char *tempptr = NULL;
   tempptr = XMLString::transcode(e.getSystemId( ));
   tmpptr = XMLString::transcode(e.getMessage( ));
   snprintf(errormsg,BUFSIZ,"\nFatal Error at file %s, line %d, char %d\n
Message: %s\n",tempptr,e.getLineNumber( ),e.getColumnNumber( ),tmpptr);
   delete tmpptr;
   delete tempptr;
   throw CommandException(errormsg);
}
//----------------------------------------
void CommandDelegate::resetErrors( )
{
    return;
}
//------------------------------------------
void CommandDelegate::processingInstruction(cons XMLCh *target,
                           const XMLCh *data)
{
    return;
}
//-----------------------------------------------
void CommandDelegate::setDocumentLocator(const class Locator *locater)
{
    return;
}
//-----------------------------------------------
void CommandDelegate::startPrefixMapping(const XMLCh *data, const XMLCh
                          *data1)
{
    return;
}
//------------------------------------------------
```

EXAMPLE 2-continued

A Procedure In A Computer Database System According to One Embodiment Of
This Disclosure For Passing Data To A Command For Processing Implemented Using C++

```
void CommandDelegate::endPrefixMapping(const XMLCh *data)
{
    return;
}
//----------------------------------------------------
void CommandDelegate::skippedEntity(const XMLCh *data)
{
    return;
}
//------------------------------------------------------------
void CommandDelegate::Initialize( )
{
   if ((strstr(mp_pCommandName->c_str( ),".so") != NULL)) {
      loadDll(mp_pCommandName->c_str( ));
   }
   else {
      //need to load the object from the IOR
      //for now will assume name is a file containing IOR
      //of object. Will then read contents of file and
      use string to object to obtain CORBA object
      char ref[BUFSIZ];
      const char *iorFile = NULL;
      struct stat buf;
      iorFile = mp_pCommandName->c_str( );
      if (strstr(iorFile,"perl") != NULL)
      {
         iorFile = loadServer( );
           /** @todo get rid of this usleep. need to have a better way to
              * verify the file exists
              */
         usleep(2000000);
      }
      if (stat(iorFile,&buf) != 0) {
         string errormsg = string("Error file: " +*mp__pCommandName+ " not
found.");
         throw CommandException(errormsg.c_str( ));
      }
      ifstream in(iorFile);
      in >>ref;
      in.close( );
      CORBA::Object_var obj = mp_pOrb->string_to_object(ref);
      if (CORBA::is_nil(obj)) {
         string errormsg = string("Error Object: " +*mp_pCommandName+ " is
NULL.");
         throw CommandException(errormsg.c_str( ));
      }
      //need to check object right here
      mp_pInterface = CommandDelegateInterface::_narrow(obj);
   }
   return;
}
//------------------------------------------------------------
char *CommandDelegate::loadServer( )
{
    /**
       * need to obtain a unique filename and pass that filename as
       * as parameter to the server being invoked. Then verify the file
       * exists before returning.
       */
    /** @todo need to switch this to fork/exec for speed increase but
       * will leave it as a system call for beta testing to show worst
       * case performance.
       */
    char *tempFileName = NULL;
    char *tempPtr = NULL;
    char *buffer = NULL;
    char executeBuffer[BUFSIZ];
    tempPtr = rindex(mp_pCommandName->c_str( ),'/');
    if (tempPtr == NULL)
        tempPtr = (char *)mp_pCommandName->c_str( );
    else
        tempPtr++;
    buffer = new char[strlen(tempPtr+15];
    sprintf(buffer,"/tmp/%sXXXXXX",tempPtr);
    tempFileName = mktemp(buffer);
    (tempFileName == NULL)
    {
```

EXAMPLE 2-continued

A Procedure In A Computer Database System According to One Embodiment Of This Disclosure For Passing Data To A Command For Processing Implemented Using C++

```
                string errormsg = string("Error could not create temp file name "+
                                    *tempFileName);
                throw CommandException(errormsg.c_str( ));
        }
        /** need to pass the buffer as a parameter to the server to be
         *   invoked
         */
        sprintf[executeBuffer,"echo %s | %s &",
                buffer,mp_pCommandName->c_str( )};
        if (system(executeBuffer) != 0)
        (
           string errormsg = string("Error Server: " +*mp_pCommandName
                                    + "didnt execute.");
           throw CommandException(errormsg.c_str( ));
        }
        return buffer;
}
string *CommandDelegate::icon( )
{
    char *tempPtr = NULL;
    tempPtr = rindex(mp_pCommandName->c_str( ),'/');
    if (tempPtr != NULL) {
       tempPtr++;
       string tempName(tempPtr);
       return new string("/omm/share/pixmaps/" + tempName + ".xpm");
    }
    return new string("/omm/share/pixmaps/" + *mp_pCommandName + ".xpm");
}
void CommandDelegate::loadDll(cons char *fname)
{
    bool symCheck = false;
    struct stat sbuf;
    if (fname == NULL){
       string errormsg = string("NULL passed as command Name");
       throw CommandException(errormsg.c_str( ));
    }
    //need to stat the file
    if (stat(fname,&sbuf) != 0){
       string errormsg = string("Command: "+ *mp_pCommandName +
                                " not found!");
       throw CommandException(errormsg.c_str( ));
    }
    //try to load the library
    mp_pVoidHandle = dlopen( fname, RTLD_NOW );
    mp_Err = dlerror( );
    if (mp_Err != NULL) {
       string errormsg = string("Error loading: "+ *mp_pCommandName +
                     " returned the following error. " + mp_Err);
       throw CommandException(errormsg.c_str( ));
    }
    //call getsymbol to load the initial function to get the object
    //of the plugin if true
    //set ptr to it else set ptr equal to null
    init_func = 0;
    if( lastError( ) == 0 ) {
       symCheck = getSymbol( (void **)&init_func,¢mico_module_init");
    }
    if (symCheck == false) {
       string errormsg = string("Error mico_module_init method in Object: "+
                          *mp_pCommandName+ " not found.");
       throw CommandException(errormsg.c_str( ));
    }
    mp_pInterface = ((CommandDelegateInterface_ptr)init_func( ));
    return;
}
bool CommandDelegate::getSymbol(void **v,const char *sym_name)
{
    if( mp_pVoidHandle != 0) {
       *v = dlsym(mp_pVoidHandle, sym_name );
       mp_Err = dlerror( );
       return (mp_Err == 0);
    }
    return false;
}
void CommandDelegate::unLoadSymbol( )
{
    //this is for remote perl servers
```

EXAMPLE 2-continued

A Procedure In A Computer Database System According to One Embodiment Of This Disclosure For Passing Data To A Command For Processing Implemented Using C++

```
if (mp_pInterface != NULL) {
    if (strstr(mp_pCommandName->c_str( ),"perl") != NULL)
    {
        try
        {
            mp_pInterface->exit( );
        }
        catch (CORBA::Exception &ex) {
            string errormsg=string("Error Object: " + *mp_pCommandName + " is
inaccessible.");
            throw CommandException(errormsg.c_str( ));
        }
    }
    CORBA::release(mp_pInterface);
}
if (mp_pVoidHandle != NULL || mp_pVoidHandle != 0) {
    dlclose(mp_pVoidHandle);
}
mp_pVoidHandle = NULL;
mp_pInterface = NULL;
return;
}
```

EXAMPLE 3

A Procedure In A Computer Database System According to One Embodiment Of This Disclosure For Retrieving And Aligning Single Molecule Restriction Maps Implemented Using C++

```
#include <iostream>
#include <vector>
#include <string>
#include <CORBA-SMALL.h>
#include <limits.h>
#include <mico/template_impl.h>
#include <gtk/gtk.h>
#include <gnome.h>
#include <stdio.h>
#include "libomm/GnommUtils.hpp"
#include "libomm/InfoParse.hpp"
#include "libommdb/DbUtil.hpp"
#include "AlignGetMaps.hpp"
AlignGetMaps::AlignGetMaps( )
{
    /*initialize database connection */
    DbUtil dbutil;
    mp_dbHandle = dbutil.connect( );
    return;
}
AlignGetMaps::~AlignGetMaps( )
{
    disconnect_DB(mp_dbHandle);
}
char *AlignGetMaps::identity( )
{
    return strdup("Aligned Getmaps");
}
CORBA::Short AlignGetMaps::type( )
{
    //type two is for command delegates.
    return 2;
}
char *AlignGetMaps::help( )
{
    return strdup("AlignGetMaps command delegate help");
}
//-----------------------------------------------
CORBA::Short AlignGetMaps::preProcess( )
{
    //first called, pop up a GUI, before data is sent to me
    loadGladeInterface( );
    return 0;
}
CORBA::Short AlignGetMaps::endDocument( )
{
```

EXAMPLE 3-continued

A Procedure In A Computer Database System According to One Embodiment Of This Disclosure For Retrieving And Aligning Single Molecule Restriction Maps Implemented Using C++

```cpp
    //third and last call,
    //first query the database to get the other fields needed
    query( );
    //then run dialog to determine output method
    runOutputDialog( );
    return 0;
    //component will be destroyed next
}
CORBA::Short AlignGetMaps::addRow(const StringSeq& fields,
                                   const StringSeq& singleRow)
{
    //second call,   serialized data
    CORBA::Short  status=0;
    if (fields.length( ) !=singleRow.length( ))
    {
        cerr <<"ERROR Vector sizes don't match\n";
        return −1;
    }
    contigrunIdVector.push_back(string(singleRow[0].in( )));
    return status;
}
//--------------------------------------------------
CORBA::Long AlignGetMaps::getMin( )
{
    return 1;
}
CORBA::Long AlignGetMaps::getMax( )
{
        return INT_MAX;
}
StringSeq *AlignGetMaps::queryFields( )
{
    StringSeq fields;
    fields.length(1);
    fields[0] = (const char *)"contigrun.contigrun_id";
    StringSeq* result = new StringSeq;
    *result = fields;
    return result;
}
void AlignGetMaps::parameters(const char *paramVals)
{
    cout <<"parameters: "<<paramVals<<endl;
    return;
}
//-----------------------------------------------------
//Do NOT EDIT SOURCE BELOW THIS LINE
//-----------------------------------------------------
static CommandDelegateInterface_ptr server = CommandDelegateInterface::_nil( );
extern "C" CommandDelegateInterface_ptr
mico_module_init( )
{
    // if (strcmp(version,MICO_VERSION))
    //    return FALSE;
    //CORBA::ORB::ObjectTag_var tag = CORBA::ORB::string_to_tag ("bread");
    server=new AlignGetMaps;
    return server;
}
//--------------------------------------------------------
//Do NOT EDIT SOURCE ABOVE THIS LINE
//-----------------------------------------------------
/**********************************************************
*
* Component specific code
*
**********************************************************/
void AlignGetMaps::loadGladeInterface( )
{
    //preprocess widgets
    gladeHandle1 = new
GladeInterface("/omm/share/glade/groupgetmaps.glade","Process");
    mainFrameWidget        = gladeHandle1->GladeInterfaceGetWidget("Process");
    lastRunRadio           = gladeHandle1->GladeInterfaceGetWidget("lastRunRadio");
    specificRunRadio       = gladeHandle1-
>GladeInterfaceGetWidget("specificRunRadio");
    runEntry               = gladeHandle1->GladeInterfaceGetWidget("runEntry");
    allowManualCheck       = gladeHandle1-
>GladeInterfaceGetWidget("allowManualCheck");
```

EXAMPLE 3-continued

A Procedure In A Computer Database System According to One Embodiment Of This Disclosure For Retrieving And Aligning Single Molecule Restriction Maps Implemented Using C++

```
    allowSemiautoCheck      = gladeHandle1-
>GladeInterfaceGetWidget("allowSemiautoCheck");
    allowAutoCheck          = gladeHandle1-
>GladeInterfaceGetWidget("allowAutoCheck");
    postprocess widgets
    gladeHandle2 = new
GladeInterface("/omm/share/glade/groupgetmaps.glade","OutputDialog");
    saveFrameWidget         = gladeHandle2->GladeInterfaceGetWidget("OutputDialog");
    numMapsLabel            = gladeHandle2->GladeInterfaceGetWidget("numMapsLabel");
    mapsetNameEntry         = gladeHandle2-
>GladeInterfaceGetWidget("mapsetNameEntry");
    saveDBRadio             = gladeHandle2->GladeInterfaceGetWidget("saveDBRadio");
    saveFileRadio           = gladeHandle2->GladeInterfaceGetWidget("saveFileRadio");
    mp_pProjectList         = gladeHandle2->GladeInterfaceGetWidget("projectmenu");
    mp_pNotesEntry          = gladeHandle2->GladeInterfaceGetWidget("notesEntry");
    avgMolSizeLabel         = gladeHandle2->GladeInterfaceGetWidget("avgmolsize");
    avgFragSizeLabel        = gladeHandle2->GladeInterfaceGetWidget("avgfragsize");
    totalSizeLabel          = gladeHandle2->GladeInterfaceGetWidget("totalsize");
    GtkWidget *fileEntryFrame = gladeHandle2-
>GladeInterfaceGetWidget("fileEntryFrame");
    mapsetPathEntry         = gnome_ file_entry_new(NULL, _("Select maps
file"));
    gnome_file_entry_set_modal(GNOME_FILE_ENTRY(mapsetPathEntry),TRUE);
    gtk_container_add (GTK_CONTAINER(fileEntryFRAME), mapsetPathEntry);
    buildProjectMenu( );
}
void AlignGetMaps::query(void)
{
    /**
     * given the list of mapids. run a query on each to get the map and name
     */
    GString     *queryString = g_string_new("");
    int         numRowsReturned, num Fields;
    int         map_id;
    char        **currentRow=NULL;
    char contigrunID(37);
    printf("query on %d contigRuns\n",contigrunIdVector.size( ));
    for(int i=0;i;21 (int)contigrunIdVector.size( );i'30 '30 ) (
        strncpy(contigrunId,contigrunIdVector[i].c_str( ),37);
        /** building the query */
        g_string_truncate(queryString,0);
        q_string_append(queryString, "select ");
        q_string_append(queryString, "aligned_maps.restriction_maps_id ");
        q_string_append(queryString, "FROM contig_island, aligned_maps ");
        q_string_append(queryString, "WHERE");
        q_string_append(queryString,
"aligned_maps.contig_island.id=contig_island.contig.island_id AND ");
        g_string_sprintfa(queryString, "contig_island.contigrun_id='%s' ",
contigrunID);
        q_string_append(queryString, ";");
        //printf(" query='/n", queryString->str);
        // submit the query to the database
        if (query_DB(mp_dbHandle,queryString->str)==0) {
            numRowsReturned = number_Rows_DB(mp_dbHandle);
            numFields       = number_Fields_DB(mp_dbHandle);
            //printF("    %d rows , %d fields, returned\n", numRowsReturned,
numFields);
            while(numRowsReturned>0) {
                currentRow=fetch_Next_Row_DB(mp_dbHandle);
                numRowsReturned--;
                map_id = atoi (currentRow[0]);
                mapset.addMap(map_id);
            )
            free_Result_DB(mp_dbHandle);
        }
        else {
            cerr <<"error calling query\n";
        }
    }
    mapset.checkMapset( );
    mapset.printMapsetStats( );
    return;
}
int AligGetMaps::runOutputDialog( )
{
    int                 status=0;
    GtkWidget           *dialog;
```

EXAMPLE 3-continued

A Procedure In A Computer Database System According to One Embodiment Of This Disclosure For Retrieving And Aligning Single Molecule Restriction Maps Implemented Using C++

```
    char                *buffer=NULL;
    char                message[BUFSIZ];
    int                 numMaps = mapset.getNumMaps( );
    int                 totalFragmentCount = mapset.getTotalFragmentCount( );
    double              totalMass = mapset.getTotalMass( );
    //printf("OUTPUT %d maps selected\n", numMaps);
    if(numMaps==0) return 0;
    sprintf(message,"Gentigrun level Getmaps");
    dialog=gnome_dialog_new(message,
                            GNOME_STOCK_BUTTON_OK,
                            GNOME_STOCK_BUTTON_CANCEL,
                            NULL);
    gnome_dialog_set_close(GNOME_DIALOG(dialog),FALSE);
    gtk_container_add (GTK_CONTAINER (GNOME_DIALOG(dialog)->)vbox),
saveFrameWidget);
    gtk_window_set_default_size(GTK_WINDOW(GNOME_DIALOG(dialog)),500,200);
    sprintf(message,"%d", numMaps);
    gtk_label_set_text(GTK_LABEL(numMapsLabel), message);
    sprintf(message, "%.2f", (totalMass/(double)numMaps));
    gtk_label_set_text(GTK_LABEL(avgMolSizeLabel),message);
    sprintf(message,"%.2f", (totalMass/(double)totalFragmentCount));
    gtk_label_set_text(GTK_LABEL(avgFragSizeLabel),message);
    sprintf(message,"%.2f",totalMass/(double)1000);
    gtk_label_set_text(GTK_LABEL(totalSizeLabel),message);
    gtk_widget_show_all(saveFrameWidget);
    //
    // now run the dialog panel
    //
    status-gnome_dialog_run(GNOME_DIALOG(dialog));
    //printf("dialog status=%d\n", status);
    //
    // do the saves
    //
    getProjectName( );
    if (status==0) {
        if(gtk_toggle_button_get_active(GTK_TOGGLE_BUTTON(saveDBRadio))) {
            gchar *TempChars =
gtk_editable_get_chars(GTK_EDITABLE(mapsetNameEntry), 0, -1);
            char *usernotes = gtk_editable_get_chars(GTK_EDITABLE(mp_pNotesEntry),
0, -1);
            printf("save to DB mapset = '%s'\n", tempChars);
            mapset.saveMapsToDBWithName((const char *)tempChars, (const char
*)usernotes);
        }
        else if(gtk_toggle_button_get_active(GTK_TOGGLE_BUTTON(saveFileRadio))) {
            //gchar *tempChars =
gtk_editable_get_chars(GTK_EDITABLE(mapsetPathEntry), 0, -1);
            gchar *tempChars =
gnome_file_entry_get_full_path(GNOME_FILE_ENTRY(mapsetPathEntry), false);
            mapset.saveMapsToPath(tempChars);
        }
    }
    gtk_widget_destroy(dialog);
    return status;
}
void AlignGetMaps::buildProjectMenu( )
{
    // mp_pProjectList
        GtkWidget *menu;
    DbUtil mydb;
    GtkWidget *curItem;
    vector<string> *projList = NULL;
    //make a menu
    menu = gtk_menu_new( );
    projList = mydb.getListOfProjects(mp_dbHandle);
    if (projList != NULL){
        if (projList->empty( ) == false){
            for (int i = 0; i < projList->size( ); i++){
                curItem = gtk_menu_item_new_with_label(projList-
>operator[ ](i).c_str( ));
                gtk_widget_set_name(curItem,\
                                    (const char *)projList->operator[ ](i).c_str( ));
                gtk_menu_append (GTK_MENU (menu), curItem);
            }
        }
    }
    gtk_option_menu_set_menu(GTK_OPTION_MENU(mp_+13pProjectList),menu);
```

EXAMPLE 3-continued

A Procedure In A Computer Database System According to One Embodiment Of This Disclosure For Retrieving And Aligning Single Molecule Restriction Maps Implemented Using C++

```
    gtk_menu_set_active(GTK_MENU (menu),0);
    delete projList;
    return;
}
string;
AlignGetMaps::getProjectName( )
{
    //this method gets the currently selected project from the project list
    //mp_pProjectList
    GtkWidget *menu;
    char *curStr = NULL;
    string *project = NULL;
    GtkWidget *currentItem = NULL;
    menu = gtk_option_menu_get_menu(GTK_OPTION_MENU(mp_pProjectList));
    currentItem = gtk_menu_get_active (GTK_MENU(menu));
    if (currentItem !=NULL) {
       curStr = gtk_widget_get_name(currentItem);
       if (curStr != NULL)
          project = new string(curStr);
    }
    mapset.setProjectName(project->c_str( ));
    return project;
}
```

EXAMPLE 4

A Procedure In A Computer Database System According to One Embodiment Of This Disclosure For Managing Various Data Views Implemented Using C++

```
#include <glob.h>
#include <gtk/gtk.h>
#include <gtk/gtkmain.h>
#include <gnome.h>
#include <exception>
#include <gal/e-paned/e-hpaned.h>
#include "libwidgets/e-shell-folder-title-bar.h"
#include "libomm/Glob.hpp"
#include "ViewManager.hpp"
#include "DBView.hpp"
#include "ActionCommand.hpp"
#include "CommandDelegate.hpp"
#include "DocumentException.hpp"
#include "libomm/CommandException.hpp"
#include "stdexcept>
static void quit(GtkWidget *window, GdkEvent *event, gpointer data);
static void toolbarCallback(GtkWidget *toolbar, gpointer data);
static void viewMenuCallback(GtkWidget *widget,gpointer data);
static void populateInterface(GtkWidget *widget, gpointer data);
static int idleCallback(gpointer data);
static void HelpContentsCallback(GtkWidget *widget,gpointer data);
static void aboutCallback(GtkWidget *widget,gponter data);
ViewManager* ViewManager::_instance = NULL;
ViewManager::ViewManager( )
{
    // Shouldn't be here.
}
ViewManager::viewManager(const string &xmlpath, int argc, const char **argv)
     : m_idleOn(false), mp_pCurrentView(NULL), mp_pCommandFactory(NULL),
       mp_pCurrentToolvar(NULL),mp_pMainMenu(NULL)
{
    m_XmlPath = xmlpath;
    /** these two calls create two cursors a normal one and a busy one */
    mp_pNormalCursor = gdk_cursor_new(GDK_LEFT_PTR);
    mp_pBusyCursor =0 gdk_cursor_new(GDK_WATCH);
    loadCommandFactory(argc, argv);
    builMainApp( );
}
ViewManager::-ViewManager( )
{
    gtk_widget_destroy(mp_pAppWindow);
    for (map<string, View*>::const_iterator i = mp_ViewList.begin( );
            i != mp_ ViewList.end( ); i++) {
       delete i->second;
    }
```

EXAMPLE 4-continued

A Procedure In A Computer Database System According to One Embodiment Of This Disclosure For Managing Various Data Views Implemented Using C++

```
   mp_ViewList.clear( );
   /** @todo need to delete notebook widget? */
   for (map<string,GnomeUIInfo*>::const_iterator i= mp_UIInfo.begin( );
            != mp_UIInfo.end( );i++){
      delete [ ] i->second;
   }
   for (map<string,GnomeUIInfo*>::const_iterator i= mp_UIInfom.begin( );
            i!= mp_mpUIInfom.end( );i++){
        delete [ ] i->second;
   }
   delete mp_pCommandFactory;
   delete mp_pShortcuts;
   delete [ ] mp_pSubViews;
   delete [ ] mp_pHelpMenu;
   delete [ ] mp_pFileSubMenu;
   delete [ ] mp_pEmptyMenu;
   delete [ ] mp_pMenuUIInfo;
}
ViewManager* ViewManager::instance(void)
{
   return _instance;
}
ViewManager* ViewManager::instance(const string &xmlpath, int argc, const char
**argv)
{
   if (_instance == NULL) {
      _instance = new ViewManager(xmlpath, argc, argv);
   }
   return _instance;
}
void ViewManager::buildMainApp( )
{
   //removed these two lines cause it we need this program
   //to be displayable on the suns.!!!!!!!!!!!!!!
   //gtk_widget_push_visual(gdk_rgb_get_visual( ));
   //gtk_widget_push_colormap(gdk_rgb_get_cmap( ));
   mp_pAppWindow = gnome_app_new("OmmCraft",
                          "OmmCraft");
   gtk_window_set_default_size(GTK_WINDOW(mp_pAppWindow), 800, 600);
   gtk_window_set_policy(GTK_WINDOW(mp_pAppWindow), FALSE, TRUE, FALSE);
   mp_pStatusBar = gnome_appbar_new(TRUE, TRUE, GNOME_PREFERENCES_NEVER);
   gnome_appbar_set_default(GNOME_APPBAR(mp_pStatusBar), "Ready.");
   gnome_app_set_statusbar(GNOME_APP(mp_pAppWindow), mp_pStatusBar);
   mp_pProgressBar = gnome_appbar_get_get_progress(GNOME_APPBAR(mp_pStatusBar));
   gtk_signal_connect(GTK_OBJECT(mp_pAppWindow), "delete-event",
               GTK_SIGNAL_FUNC(quit), NULL);
   gtk_signal_connect(GTK_OBJECT(mp_pAppWindow), "show",
               GTK_SIGNAL_FUNC(populateInterface), NULL);
   // Create horizontal pane that will seperate View and shorcut bar
   GtkWidget *hpaned = e_hpaned_new( );
   e_paned_set_handle_size(E_PANED(hpaned), 5);
   gtk_container_set_border_width(GTK_CONTAINER(hpaned), 5);
   gtk_widget_show(hpaned);
   gnome_app_set_contents(GNOME_APP(mp_pAppWindow), hpaned);
   // Create shortcut model and widget
   GtkWidget* frame = gtk_frame_new(NULL);
   gtk_frame_set_shadow_type(GTK_FRAME(frame), GTK_SHADOW_IN);
   gtk_widget_show(frame);
   mp_pShortcuts = new Shortcuts( );
   mp_pShortcutbar = mp_pShortcuts->getShortcutBar( );
   gtk_widget_show(mp_pShortcutbar);
   gtk_container_add(GTK_CONTAINER(frame), mp_pShortcutbar);
   addGroups( );
   e_paned_pack1(E_PANED(hpaned), frame, TRUE, TRUE);
   e_paned_set_position(E_PANED(hpaned), 100);
   // Create shell
   frame = gtk_frame_new(NULL);
   gtk_frame_set_shadow_type(GTK_FRAME(frame), GTK_SHADOW_IN);
   gtk_widget_show(frame);
   mp_pPackBow = gtk_vbox_new(FALSE, 0);
   gtk_container_add(GTK_CONTAINER(frame), mp_pPackBox);
   gtk_widget_show(mp_pPackBox);
   e_paned_pack2(E_PANED(hpaned), frame, TRUE, FALSE);
   mp_pTitleBar = e_shell_folder_title_bar_new( );
   e_shell_shell_folder_title_bar_set_title(E_SHELL_FOLDER_TITLE_BAR(mp_pTitleBar),
"None");
   gtk_widget_show(mp_pTitleBar);
```

EXAMPLE 4-continued

A Procedure In A Computer Database System According to One Embodiment Of This Disclosure For Managing Various Data Views Implemented Using C++

```
    gtk_box_pack_start(GTK_BOX(mp_pPackBox), mp_pTitleBar, FALSE, TRUE, 0);
    gtk_widget_pop_visual( );
    gtk_widget_pop_colormap( );
}
    void ViewManager::show(void)
    {
        gtk_widget_show(mp_pAppWindow);
    }
    void ViewManager::checkResources( )
    {
      //** @todo Implement checkResources. */
    }
    void ViewManager::loadToolBar(const string&uri)
    {
      if(mp_pCurrentToolbar) {
        gtk_widget_hide(mp_pCurrentToolbar);
      )
      // get the toolbar if there is one
      if (mp_Toolbars[uri]) {
        mp_pCurrentToolbar = mp_Toolbars[uri];
        gtk_widget_show(mp_pCurrentToolbar);
      )
      else {
        // there isn't a toolbar.. make it
        vector<Command*>* commands = mp_pCurrentView->getCommands( );
        unsigned int size = commands->size( );
        GtkWidget* toolbar = gtk_toolbar_new(GTK_ORIENTATION_HORIZONTAL,
GTK_TOOLBAR_ICONS);
      if (size) {
        GnomeUIInfo *uiInfo,*uiInfom;
        //GnomeUIInfo *unInfo = new GnomeUIInfo[commands->size( )+1);
        mp_UIInfo(uri)=new GnomeUIInfo(commands->size( )+1);
        uiInfo=mp_UIInfo(uri);
        mp_UIInfo(uri)=new GnomeUIInfo(commands)->size( )+1);
        uiInfom=mp_UIInfom(uri);
        /** @todo Should be using _PIXMAP_DATA value for pixmap_type
* but using it causes ommcraft to crash. Switched back to PIXMAP_STOCK
* and program works fine. Need to figure out why this is happening
*/
        for (unsigned int i = 0; i < size; i++) {
        Command* currCommand = (*commands)[i];
        uiInfo[i].type = GNOME_APP_UI_ITEM;
            uiInfom[i].type= GNOME_APP_UI_ITEM;
            string* tempStr = currCommand->identity( );
            uiInfo[i].label = strdup(tempStr->c_str( ));
            uiInfom[i].label= strdup(tempStr->c_str( ));
            //delete tempStr;
        //tempStr = currCommand->help( );
            uiInfo[i].hint = strdup(tempStr->c_str( ));
            uiInfom[i].hint= strdup(tempStr->c_str( ));
        delete tempStr;
    uiInfo[i].moreinfo = (void *)toolbarCallback;
      uiInfom[i].moreinfo= (void *)toolbarCallback;
      uiInfom[i].user_data= currCommand;
      uiInfo[i].user_data = currCommand;
      uiInfom[i].unused_data=NULL;
      uiInfo[i].unused_data = NULL;
      uiInfom[i].pixmap_type=GNOME_APP_PIXMAP_NONE;
      uiInfo[i].pixmap_type=GNOME_APP_PIXMAP_STOCK;
    tempStr = currCommand->icon( );
    uiInfo]i .pixmap_info = strup(tempStr->c_str( ));
      uiInfom[i].pixmap_info=NULL;
      delete tempStr;
    uiInfo[i].accelerator_key = 0;
      uiInfom[i].accelerator_key =0;
      uiInfo[i].ac_mods = GDK_CONTROL_MASK;
      uiInfom[i].ac_mods=GDK_CONTROL_MASK;
      uiInfom[i]widget=NULL;
      uiInfo[i].widget = NULL;
    }
    //uiInfo[size]= GNOMEUIINFO_END;
    uiInfo[size].type = GNOME_APP_UI_ENDOFINFO;
    uiInfo[size].label = NULL;
    uiInfo[size].hint = NULL;
    uiInfo[size].moreinfo = NULL;
    uiInfo[size].user_data = NULL;
    uiInfo[size].unused_data = NULL;
```

EXAMPLE 4-continued

A Procedure In A Computer Database System According to One Embodiment Of
This Disclosure For Managing Various Data Views Implemented Using C++

```
        uiInfo[size].pixmap_type = (GnomeUIPixmapType) 0;
        uiInfo[size].pixmap_info = NULL;
        uiInfo[size].accelerator_key = 0;
        uiInfo[size].ac_mods = (GdkModifierType) 0;
        UiInfo[size].widget = NULL;
        uiInfom[size].type = GNOME_APP_UI_ENDOFINFO;
        uiInfom[size].label = NULL;
        uiInfom[size].hint = NULL;
        uiInfom[size].moreinfo = NULL;
        uiInfom[size].user_data = NULL;
        uiInfom[size].unused_data = NULL;
        uiInfom[size].pixmap_type = (GnomeUIPixmapType) 0;
        uiInfom[size].pixmap_info = NULL;
        uiInfom[size].accelerator_key = 0;
        uiInfom[size].ac_mods = (GdkModifierType) 0;
        uiInfom[size].widget = NULL;
        gnome_app_fill_toolbar(GTK_TOOLBAR(toolbar), uiInfo, NULL);
    }
gnome_app_set_toolbar(GNOME_APP(mp_pAppWindow), GTK_TOOLBAR(toolbar));
mp_Toolbars[uri]= toolbar->parent;
        mp_pCurrentToolbar = mp_Toolbars[uri];
        }
    }
}
void ViewManager::loadMenu( )
{
    GnomeUIInfo *uiInfo = NULL;
    /** @todo should clean this up in future **/
    int i = 0;
    if (!mp_pMainMenu){
        mp_pMainMenu = gtk_menu_bar_new( );
        submenu of file
        loadFileSubMenu( );
        /////////////////////////////////
        //file top menu
        mp_pMenuUIIfo = new GnomeUIInfo[5];
        uiInfo = mp_pMenuUIInfo;
        uiInfo[i].type = GNOME_APP_UI_SUBTREE;
        uiInfo[i].label = (gchar *)"File";
        uiInfo[i].hint = NULL;
        uiInfo[i].moreinfo = mp_pFileSubMenu;
        uiInfo[i].user_data = NULL;
        uiInfo[i].unused_data = NULL;
        uiInfo[i].pixmap_type = (GnomeUIPixmapType)0;
        uiInfo[i].pixmap_info = NULL;
        uiInfo[i].accelerator_key = 0;
        uiInfo[i].ac_mods = GDK_CONTROL_MASK;
        uiInfo[i].widget = NULL;
        i = 1;
        loadViewsSubMenu( );
        //views top menu
        uiInfo[i].type = GNOME_APP_UI_SUBTREE;
        uiInfo[i].label = (gchar *)"Views";
        uiInfo[i]hint = NULL;
        uiInfo[i].moreinfo = mp_pSubViews;
        uiInfo[i].user_data = NULL;
        uiInfo[i].unused_data = NULL;
        uiInfo[i].pixmap_type = (GnomeUIPixmapType)0;
        uiInfo[i].pixmap_info = NULL;
        uiInfo[i].accelerator_key = 0;
        uiInfo[i].ac_mods = GDK_CONTROL_MASK;
        uiInfo[i].widget = NULL;
        mp_pEmptyMenu = new GnomeUIInfo[1];
        mp_pEmptyMenu[0].type = GNOME_APP_UI_ENDOFINFO;
        mp_pEmptyMenu[0].label = NULL;
        mp_pEmptyMenu[0].hint = NULL;
        mp_pEmptyMenu[0].moreinfo = NULL;
        mp_pEmptyMenu[0].user_data = NULL;
        mp_pEmptyMenu[0].unused_data = NULL;
        mp_pEmptyMenu[0].pixmap_type = (GnomeUIPixmapType) 0;
        mp_pEmptyMenu[0].pixmap_info = NULL;
        mp_pEmptyMenu[0].accelerator_key = 0;
        mp_pEmptyMenu[0].ac_mods = (GdkModifierType) 0;
        mp_pEmptyMenu[0].widget = NULL;
        i = 2;
        uiInfo[i].type = GNOME_APP_UI_SUBTREE;
        uiInfo[i].label = (gchar *)"Commands";
        uiInfo[i].hint = NULL;
```

EXAMPLE 4-continued

A Procedure In A Computer Database System According to One Embodiment Of This Disclosure For Managing Various Data Views Implemented Using C++

```
    uiInfo[i].moreinfo = mp_pEmptyMenu;
    uiInfo[i].user_data = NULL;
    uiInfo[i].unused_data = NULL;
    uiInfo[i].pixmap_type = (GnomeUIPixmapType)0;
    uiInfo[i].pixmap_info = NULL;
    uiInfo[i].accelerator_key = 0;
    uiInfo[i].ac_mode = GDK_CONTROL_MASK;
    uiInfo[i].widget = NULL;
    loadHelpMenu;
    i = 3;
    uiInfo[i].type = GNOME_APP_UI_SUBTREE;
    uiInfo[i].label = (gchar *)"Help";
    uiInfo[i].hint = NULL;
    uiInfo[i].moreinfo = mp_pHelpMenu;
    uiInfo[i].user_data = NULL;
    uiInfo[i].unused_data = NULL;
    uiInfo[i].pixmap_type = (GnomeUIPixmapType)0;
    uiInfo[i].pixmap_info = NULL;
    uiInfo[i].accelerator_key = 0;
    uiInfo[i].ac_mods = GDK_CONTROL_MASK;
    uiInfo[i].widget = NULL;
    i = 4;
    //**terminating uinfo
    uiInfo[i].type = GNOME_APP_UI_ENDOFINFO;
    uiInfo[i].label = NULL;
    uiInfo[i].hint = NULL;
    uiInfo[i].moreinfo = NULL;
    uiInfo[i].user_data = NULL;
    uiInfo[i].unused_data = NULL;
    uiInfo[i].pixmap_type = (GnomeUIPixmapType) 0;
    uiInfo[i].pixmap_info = NULL;
    uiInfo[i].accelerator_key = 0;
    uiInfo[i].ac_mods = (GdkModifierType) 0;
    uiInfo[i].widget = NULL;
    //end of file menu
    gnome_app_fill_menu(GTK_MENU_SHELL(mp_pMainMenu),
uiInfo,GNOME_APP(mp_pAppWindow)->accel_group,false,]);
    gnome_app_set_menus(GNOME_APP(mp_pAppWindow),GTK_MENU_BAR(mp_pMain-
Menu));
    /** @todo need to fix this. calling this remove to get rid of gnome
submenu's
     * in help menu
     */
    gnome_app_remove_menus(GNOME_APP(mp_pAppWindow),"Help/",5);
    gnome_app_insert_menus(GNOME_APP(mp_pAppWindow),"Help/",mp_pHelpMenu);
  }
}
void ViewManager::loadViews(void)
{
  string pattern("*.xml");
  Glob xmlGlob(m_XmlPath, pattern);
  int size = xmlGlob.size( );
  for (int i = 0; i < size; i++) {
    string *match = xmlGlob.getMatch(i);
    string viewFile(*match);
    delete match;
    string statusMsg("Loading " ++viewFile);
    try {
      pushStatusBar(statusMsg);
      DBView *newView = new DBView(viewFile, *mp_pCommandFactory);
      /** @todo Change calls to getName to getURI. */
      mp_ViewList(*newView->getName( )) = newView;
      popStatusBar( );
      mp_pShortcuts->addShortcut(*newView->getName( ),
                                 *newView->getShortcut( ),
                                 *newView->getName( ),
                                 *newView->getIcon( ));
    }
    catch (DocumentException &e) {
      string errorMsg("There was an error loading the view contained in the
file ");
      gnome_warning_dialog_parented(errorMsg.c_str( ),
GTK_WINDOW(mp_pAppWindow( );
      popStatusBar( );
    }
  }
  loadMenu( );
```

EXAMPLE 4-continued

A Procedure In A Computer Database System According to One Embodiment Of This Disclosure For Managing Various Data Views Implemented Using C++

```
}
void ViewManager::loadCommandFactory(int argc, const char **argv)
{
   mp_pCommandFactory = new CommandFactory(argc, argv);
}
void ViewManager::setCurentView(const string &uri)
{
   GtkWidget *viewWidget;
   if (mp_pCurrentView == mp_ViewList[uri]) {
      return;
   }
   setCursorBusy( );
   if (mp_pCurrentView) {
      viewWidget = mp_pCurrentView->getView( );
      gtk_conter_remove(GTK_CONTAINER(mp_pPackBox), viewWidget);
   }
   mp_pCurrentView = mp_ViewList[uri];
   viewWidget = mp_pCurrentView->getView( );
   e_shell_folder_title_bar_set_title(E_SHELL_FOLDER_TITLE_BAR(mp_pTitleBar),
mp_pCurrentView->getName( )->c_str( ));
   gtk_box_pack_start(GTK_BOX(mp_pPackBox), viewWidget, TRUE, TRUE, 2);
   loadToolBar(uri);
   loadMenu( );
   updateCommandMenu(uri);
   mp_pCurrentView->update( );
   setCursorNormal( );
}
void ViewManager::addGroups(void)
{
   mp_pShortcuts->addGroup("Groups Centric");
   mp_pShortcuts->addGroup("Run Centric");
   mp_pShortcuts->addGroup("Other");
}
void ViewManager::pushStatusBar(const string &message)
{
   gnome_appbar_push(GNOME_APPBAR(mp_pStatusBar), message.c_str( ));
}
void ViewManager::popStatusBar(void)
{
   gnome_appbar_pop(GNOME_APPBAR(mp_pStatusBar));
}
void ViewManager::setProgreeeBar(float value)
{
   gtk_progress_set_percentage(GTK_PROGRESS(mp_pProgressBar), value);
}
void ViewManager::callCommand(Command *command)
{
   if (command->type( ) ==1) {
      // This is an action command
      /** @todo Change command type checking to use either enumeration or
         something easier to maintain.*/
         /** on redhat 7.1 dynamic_cast doesnt work */
         //ActionCommand* action=dynamic_cast<Command *>(command);
         ActionCommand* action = (ActionCommand*)(command);
         try
         {
            setCursorBusy( );
            action->execute( );
            setCursorNormal( );
         }
         catch (CommandException &ex)
         {
            setCursorNormal( );
            cerr<<"Error calling command: "<<*ex.getMessage[ ]<<endl;
         }
      }
      else if (command->type( ) ==2) {
         /** on redhar 7.1 dynamic_cast doesnt work */
         CommandDelegate* delegate = (CommandDelegate*)(command);
         try
         {
            set CursorBusy( );
            mp_pCurrentView->serialize((Serializable *)delegate);
            setCursorNormal( );
         }
         catch (CommandException &ex)
         {
```

EXAMPLE 4-continued

A Procedure In A Computer Database System According to One Embodiment Of
This Disclosure For Managing Various Data Views Implemented Using C++

```
            setCursorNormal( );
            cerr <<"Error calling command: "<<*ex.getMessage( )<<end1;
        }
      }
    }
    void ViewManager::updateToolbar( )
    {
        if (mp_pCurrentView == NULL)
            return;
        vector<char> *temp = NULL;
        vector<Command*> *commandVector = NULL;
        GnomeUIInfo *uiInfo, *uiInfom;
        int j = 0;
        temp = mp_pCurrentView->getCommandStates( );
        if (temp == NULL)
            return;
        commandVector = mp_pCurrentView->getCommands( );
        if (commandVector ==NULL) {
            delete temp;
            return;
        }
        uiInfo = mp__UIInfo(*mp_pCurrentView->getName( ));
        uiInfom = mp_UIInfom(*mp_pCurrentView->getName( ));
        for (int i = 0; i<(int)commandVector->size( )+1;i++)
        (
            if (uiInfo[i].user_data == NULL || uiInfom[i].user_data == NULL)
                continue;
            if (temp->operator[ ](j) == '1'){
                gtk_widget_set_sensitive(uiInfom[i].widget,TRUE);
                gtk_widget_set_sensitive(uiInfo[i].widget,TRUE);
            }
            if (temp->operator[ ](j) == '0'){
                gtk_widget_set_sensitive(uiInfom[i].widget,FALSE);
                gtk_widget_set_sensitive(uiInfo[i].widget,FALSE);
            }
            j++;
        }
        delete temp;
        return;
    }
    void ViewManager::turnOnIdle(void)
    {
        /** need mutex */
        if (!m_idleOn) {
            m_idleOn = true;
            gtk_idle_add(idleCallback, NULL);
        }
    }
    void ViewManager::updateCurrentView( )
    {
        if (mp_pCurrentView == NULL;
            return;
        try {
            mp_pCurrentView->updateIdle( );
        }
        catch (...){
            //cerr <<"error with command: "<<*ex.getMessage( )<<end1;
            cerr <<"error with command\n";
        }
        string *tempString = mp_pCurrentView->getStatusLine( );
        if (tempString != NULL){
            gnome_appbar_pop(GNOME_APPBAR(mp_pStatusBar));
            gnome_appbar_push(GNOME_APPBAR(mp_pStatusBar), tempString->c_str( ));
            delete tempString;
        }
            else
            gnome_appbar_pop(GNOME_APPBAR(mp_pStatusBar));
    }
    void ViewManager::loadFileSubMenu( )
    {
      GnomeUIInfo *subFile = NULL;
      mp_pFileSubMenu = new GnomeUIInfo(2);
      subFile = mp_pFileSubMenu;
      subFile[0].type = GNOME_APP_UI_ITEM;
      subFile[0].label = (gchar *)"Exit";
      subFile[0].hint = NULL;
      subFile[0].moreinfo = (void *)quit;
```

EXAMPLE 4-continued

A Procedure In A Computer Database System According to One Embodiment Of
This Disclosure For Managing Various Data Views Implemented Using C++

```
    subFile[0].user_data = NULL;
    subFile[0].unused_data = NULL;
    subFile[0].pixmap_type = (GnomeUIPixmapType)0;
    subFile[0].pixmap_info = NULL;
    subFile[0].accelerator_key = 0;
    subFile[0].ac_mods = GDK_CONTROL_MASK;
    subFile[0].widget = NULL;
    subFile[1].type = GNOME_APP_UI_ENDOFINFO;
    subFile[1].label = NULL;
    subFile[1].hint = NULL;
    subFile[1].moreinfo = NULL;
    subFile[1].user_data = NULL;
    subFile[1].unused_data = NULL;
    subFile[1].pixmap_type = (GnomeUIPixmapType)0;
    subFile[1].pixmap_info = NULL;
    subFile[1].accelerator_key = 0;
    subFile[1].ac_mods = (GdkModifierType) 0;
    subFile[1].widget = NULL;
    return;
}
void ViewManager::loadViewsSubMenu( )
{
    GnomeUIInfo *subViews = NULL;
    //need to go through list of sub views and create menu item for
    //each one. also need to setup callback when that menu item is selected.
    mp_pSubViews = new GnomeUIInfo(mp_ViewList.size( )+1);
    subViews = mp_pSubViews;
    int x = 0;
    for (map<string, View*>::const_iterator i = mp_ViewList.begin( );
            i != mp_ViewList.end( ); i++) {
        subViews[x].type = GNOME_APP_UI_ITEM;
        subViews[x].label = (gchar *)9->first.c_str( );
        subViews[x].hint = NULL;
        subViews[x].moreinfo = (void *)viewMenuCallback;
        subViews[x].user_data = (gchar *)i->first.c_str( );
        subViews[x].unused_data = NULL;
        subViews[x].pixmap_type = (GnomeUIPixmapType)0;
        subViews[x].pixmap_info = NULL;
        subViews[x].accelerator_key = 0;
        subViews[x].ac_mods = GDK_CONTROL_MASK;
        subViews[x].widget = NULL;
        x++;
    }
    subViews[x].type = GNOME_APP_UI_ENDOFINFO;
    subViews[x].label = NULL;
    subViews[x].hint = NULL;
    subViews[x].moreinfo = NULL;
    subViews[x].user_data = NULL;
    subViews[x].unused_data = NULL;
    subViews[x].pixmap_type = (GnomeUIPixmapType)0;
    subViews[x].pixmap_info = NULL;
    subViews[x].accelerator_key = 0;
    subViews[x].ac_mods = (GdkModifierType) 0;
    subViews[x].widget = NULL;
    return;
}
void ViewManager::loadHelpMenu( )
{
    GnomeUIInfo *helpmenu = NULL;
    mp_pHelpMenu = new GnomeUIInfo[3];
    helpmenu = mp_pHelpMenu;
    int x = 0;
    helpmenu[x].type = GNOME_APP_UI_ITEM;
    helpmenu[x].label = (gchar *)"Contents";
    helpmenu[x].hint = NULL;
    helpmenu[x].moreinfo = (void *)HelpContentsCallback;
    helpmenu[x].user_data = NULL;
    helpmenu[x].unused_data = NULL;
    helpmenu[x].pixmap_type = (GnomeUIPixmapType)0;
    helpmenu[x].pixmap_info = NULL;
    helpmenu[x].accelerator_key = 0;
    helpmenu[x].ac_mods = GDK_CONTROL_MASK;
    helpmenu[x].widget = NULL;
    x = 1;
    helpmenu[x].type = GNOME_APP_UI_ITEM;
    helpmenu[x].label = (gchar *)"About";
    helpmenu[x].hint = NULL;
```

EXAMPLE 4-continued

A Procedure In A Computer Database System According to One Embodiment Of
This Disclosure For Managing Various Data Views Implemented Using C++

```
    helpmenu[x].moreinfo = (void *)aboutCallback;
    helpmenu[x].user_data = NULL;
    helpmenu[x].unused_data = NULL;
    helpmenu[x].pixmap_type = (GnomeUIPixmapType)0;
    helpmenu[x].pixmap_info = NULL;
    helpmenu[x].accelerator_key = 0;
    helpmenu[x].ac_mods = GDK_CONTROL_MASK;
    helpmenu[x].widget = NULL;
    x = 2;
    helpmenu[x].type = GNOME_APP_UI_ENDOFINFO;
    helpmenu[x].label = NULL;
    helpmenu[x].hint = NULL;
    helpmenu[x].moreinfo = NULL;
    helpmenu[x].user_data = NULL;
    helpmenu[x].unused_data = NULL;
    helpmenu[x].pixmap_type = (GnomeUIPixmapType)0;
    helpmenu[x].pixmap_info = NULL;
    helpmenu[x].accelerator_key = 0;
    helpmenu[x].ac_mods = GDK_CONTROL_MASK;
    helpmenu[x].widget = NULL;
    return;
}
void ViewManager::updateCommandMenu(const string &uri)
{
   //got lazy here this guy simply removes the items below the commands menu and
   //inserts the new menu
   /** @todo need to change 100 to a set correct value based on previous view command list */
   gnome_app_remove_menus(GNOME_APP(mp_pAppWindow),"Commands/",100);
gnome_app_insert_menus(GNOME_APP(mp_pAppWindow),"Commands/",mp_UIInfom(uri));
}
void ViewManager::setCursorBusy( )
{
   gdk_window_set_cursor(GTK_WIDGET(mp_pAppWindow)->window,mp_pBusyCursor);
}
void ViewManager::setCursorNormal( )
{
   gdk_window_set_cursor(GTK_WIDGET(mp_pAppWindow)->window,mp_pNormalCursor);
}
//////////////////////////////////////////////////////////////
// GTK+ Callbacks.
//////////////////////////////////////////////////////////////
static void quit(GtkWidget *window, GDKEvent *event, gpointer data)
{
      //gtk_exit(0);
      gtk_main_quit( );
}
static void toolbarCallback(GtkWidget *toolbar, gpointer data)
{
   Command* command = (Command*)data;
   ViewManager::instance( )->callCommand(command);
}
static void populateInterface(GtkWidget *widget, gpointer data)
{
   ViewManager::instance( )->loadViews( );
}
static int idleCallback(gpointer data)
{
   ViewManager::instance( )->updataCurrentView( )
   ViewManager::instance( )->updateToolbar( );
   /** if program goes multithread need mutex for this variable. */
   ViewManager::instance( )->m_idleOn = false;
   return FALSE;
}
static void viewMenuCallback(GtkWidget *widget,gpointer data)
{
   string temp = string((char *)data);
   ViewManager::instance( )->setCurrentView(temp);
   return;
}
static void HelpContentsCallback(GtkWidget *widget,gpointer data)
{
   /** @todo need to implement this **/
   cout <<"Loading Netscape to display help documentation on:\n";
   cout <<"http://alcor.lmcg.wisc.edu/projects.ommcraft/\n";
   system("netscape http://alcor.lmcg.wisc.edu/projects/ommcraft &");
```

EXAMPLE 4-continued

A Procedure In A Computer Database System According to One Embodiment Of
This Disclosure For Managing Various Data Views Implemented Using C++

```
   return;
}
static void aboutCallback(GtkWidget *widget,gpointer data)
{
   GtkWidget *about;
   const gchar *authors[ ] = {
      "Chris Churas <churas@lmcg.wisc.edu>",
      "Galex Yen <galex @lmcg.wisc.edu>",
      "Jessica Severin (icons) <jessica@lmcg.wisc.edu>",
      NULL
   };
   about = gnome_about_new (_("Ommcraft"),"1.0",
                     "© 2001 Laboratory for Molecular and Computational
Genomics",authors.
                     _(" "),
                     "/omm/share/glade/ommcraft/splash.xpm");
   gtk_window_set_modal(GTK_WINDOW(about),TRUE);
   gtk_widget_show(about);
}
```

It is to be understood that the description, specific examples and data, while indicating exemplary embodiments, are given by way of illustration and are not intended to limit the present disclosure. All references cited herein, are specifically and entirely incorporated by reference. Various changes and modifications within the present disclosure will become apparent to a skilled artisan from this disclosure, and thus are considered part of the disclosure.

It is further to be understood that the description, specific examples and data, while indicating exemplary embodiments, are given by way of illustration and are not intended to limit the invention(s) described by the appended claims. Various changes and modifications within the invention(s) defined by the appended claims will become apparent to the skilled artisan from the discussion, disclosure and data contained herein, and thus are considered part of the invention(s) described by the appended claims. In the appended claims, the articles such as "a," "an," "the" and the like can mean one or more than one, and are not intended in any way to limit the terms that follow to their singular form, unless expressly noted otherwise. Unless otherwise indicated, any claim which contains the word "or" to indicate alternatives shall be satisfied if one, more than one, or all of the alternatives denoted by the word "or" are present in an embodiment which otherwise meets the limitations of such claim.

This application claims priority to U.S. Provisional Application No. 60/447,293, filed Feb. 14, 2003, the contents of which are expressly incorporated herein by reference.

We claim:

1. A computer system for storing, processing, displaying, and analyzing single molecule data of a plurality of single molecules, the system comprising:
 a computer terminal comprising a processor;
 a display operatively connected to the processor;
 a user input device operatively connected to the processor; and
 at least one memory component in communication with the computer terminal for storing:
  a first database for storing single molecule data, wherein the single molecule data comprises image data and physical characteristic data of a corresponding single molecule, wherein the first database comprises:
   at least one restriction maps entity comprising a restriction maps ID and a runs ID;
   at least one aligned maps entity comprising said restriction maps ID;
   at least one linked maps entity comprising said restriction maps ID;
   at least one runs entity comprising said runs ID and a group ID;
   at least one flat images entity comprising said runs ID;
   at least one raw images entity comprising said group ID;
   at least one sequence entity, related to a sequence, comprising a sequence ID and a first accession value, wherein the first accession value is a first number associated to said sequence in a sequence database;
   at least one sequence contig entity, related to a sequence contig, comprising a sequence contig ID and a second accession value, wherein the second accession value is a second number associated to said sequence contig in a sequence contig database; and
  a second database for storing biomedical data, wherein the biomedical data is derived from at least one biomedical technology platform and is related to the corresponding single molecule;
 wherein the processor is programmed to execute:
  a user interface comprising:
   a plurality of containers, the containers configured to display multiple views of single molecule data, wherein at least one of the views is of all or a portion of the single molecule image data; and
   at least one control configured to receive user input,
  a view manager for controlling the user interface, the view manager being configured:
   to formulate at least one command from user input received from the at least one control;
   to receive data from a command processor for display in at least one of the containers, and to format the data received for display; and
   to serialize data displayed in at least one of the containers for use by the command processor; and
  instructions derived from the at least one command received from the view manager and configured to access the first database and the second database, the command processor returning to the view manager at least a subset of data from the single molecule data from the first database and the biomedical data from the second database corresponding to the instructions executed, the command processor further capable of receiving serialized data from the view manager, wherein the serialized data is for use with a command requiring the serialized data.

2. The system of claim 1, wherein the single molecules are nucleic acid molecules.

3. The system of claim 2, wherein the single molecules are two different nucleic acid molecules.

4. The system of claim 1, further comprising a computer network, and wherein the first database, the second database, or both are deployed over the computer network.

5. The system of claim 1, wherein the physical characteristic data of the single molecule image comprises information regarding length, height, charge density, conductivity, capacitance, resistance, sequence information, structural information and restriction map.

6. The system of claim 1, wherein the at least one command is formulated based on at least one predetermined internal instruction.

7. The system of claim 1, wherein the at least one command is formulated based on at least one instruction provided by a user.

8. The system of claim 1, wherein the image data is derived by optical mapping.

9. The system of claim 1, wherein the subset of said single molecule data is selected from the group consisting of one or more single molecule images, restriction maps, and sequences.

10. The system of claim 1, wherein the user interface comprises a first container and a second container, wherein the first container displays a different view of the single molecule image data than the second container.

11. The system of claim 1, wherein the view manager further comprises a menu and a toolbar, the toolbar comprising the at least one control.

12. The system of claim 1, wherein the single molecule data comprises a series of single molecule fragments referentially stored as contiguous such that the series of single molecule fragments forms a single molecule.

13. The system of claim 1, wherein the serialized data from the view manager is in a XML format.

14. The system of claim 1, wherein the user interface is a graphical user interface.

15. The system of claim 1, wherein the at least one control is a command line and the user input received from the control is a typed command.

* * * * *